United States Patent
Gerstmeir et al.

(10) Patent No.: US 9,347,048 B2
(45) Date of Patent: May 24, 2016

(54) FEEDBACK-RESISTANT ALPHA-ISOPROPYLMALATE SYNTHASES

(71) Applicant: EVONIK INDUSTRIES AG, Essen (DE)

(72) Inventors: Robert Gerstmeir, Werther (DE); Iris Wiegrabe, Bielefeld (DE)

(73) Assignee: Evonik Technochemie GmbH, Dossenheim (DE)

( * ) Notice: Subject to any disclaimer, the term of this patent is extended or adjusted under 35 U.S.C. 154(b) by 0 days.

(21) Appl. No.: 14/385,876

(22) PCT Filed: Apr. 12, 2013

(86) PCT No.: PCT/EP2013/057660
§ 371 (c)(1),
(2) Date: Sep. 17, 2014

(87) PCT Pub. No.: WO2013/160124
PCT Pub. Date: Oct. 31, 2013

(65) Prior Publication Data
US 2015/0079641 A1 Mar. 19, 2015

(30) Foreign Application Priority Data
Apr. 27, 2012 (DE) .......................... 10 2012 207 097

(51) Int. Cl.
*C12N 9/10* (2006.01)
*C12N 1/20* (2006.01)
*C12N 15/74* (2006.01)
(Continued)

(52) U.S. Cl.
CPC ................ *C12N 9/1025* (2013.01); *C12N 1/20* (2013.01); *C12N 15/74* (2013.01); *C12N 15/77* (2013.01); *C12P 7/40* (2013.01); *C12P 7/62* (2013.01);
(Continued)

(58) Field of Classification Search
None
See application file for complete search history.

(56) References Cited

U.S. PATENT DOCUMENTS

| 3,865,690 A | 2/1975 | Okumura et al. |
| 3,970,519 A | 7/1976 | Tsuchida et al. |
| 6,403,342 B1 * | 6/2002 | Gusyatiner .......... C12N 9/1025 435/116 |

FOREIGN PATENT DOCUMENTS

| EP | 1067191 A2 | 1/2001 |
| EP | 1860193 A1 | 11/2007 |

(Continued)

OTHER PUBLICATIONS

International Preliminary Report on Patentability and Written Opinion issued Nov. 6, 2014 in PCT/EP2013/057660.
(Continued)

*Primary Examiner* — Robert Mondesi
*Assistant Examiner* — Richard Ekstrom
(74) *Attorney, Agent, or Firm* — Reed Smith LLP; Eric J. Evain; Ryan P. Cox

(57) ABSTRACT

The invention relates to an isolated nucleotide sequence encoding an amino acid sequence that is at least ≥90%, ≥92%, ≥94%, ≥96%, ≥97%, ≥98%, ≥99% or 100%, preferably ≥97%, particularly preferably ≥98%, very particularly preferably ≥99%, and extremely preferably 0%, identical to the amino acid sequence of SEQ ID NO:2, wherein SEQ ID NO:2, at position 553, or at a corresponding position of the amino acid sequence, has a proteinogenic amino acid other than L-tyrosine, to a microorganism comprising the nucleotide sequence and also to a process for producing fine chemicals using this microorganism.

19 Claims, 1 Drawing Sheet

Map of the plasmid pK18mobsacB_leuA_Y553D

(51) Int. Cl.
*C12N 15/77* (2006.01)
*C12P 7/40* (2006.01)
*C12P 13/06* (2006.01)
*C12P 7/62* (2006.01)

(52) U.S. Cl.
CPC ......... *C12P 13/06* (2013.01); *C12Y 203/03013* (2013.01); *Y02P 20/52* (2015.11)

(56) References Cited

FOREIGN PATENT DOCUMENTS

| WO | WO-2008/098227 A2 | 8/2008 |
| WO | WO-2010/139527 A2 | 12/2010 |

OTHER PUBLICATIONS

Miroslaw Patek et al., "Leudine synthesis in *Corynebacterium glutamicum*: Enzyme Activities, Structure of *leuA*, and Effect of *leuA* Inactivation on Lysine Synthesis", Applied and Environmental Microbiology, Jan. 1994, vol. 60, No. 1, p. 133-140.

Tomoki Azuma et al., Enzymatic Background for the Reversion or Stabilization of an L-Leucine Producing Strain of *Corynebacterium glutamicum* Agric. Biol. Chem., 52 (6), 1535-1528, 1988.

Patek, M. et al., "C. glutamicum gene leuA for isopropylmalate synthase", GenBank. X70959.1, Nov. 14, 2006.

* cited by examiner

Map of the plasmid pK18mobsacB_leuA_Y553D
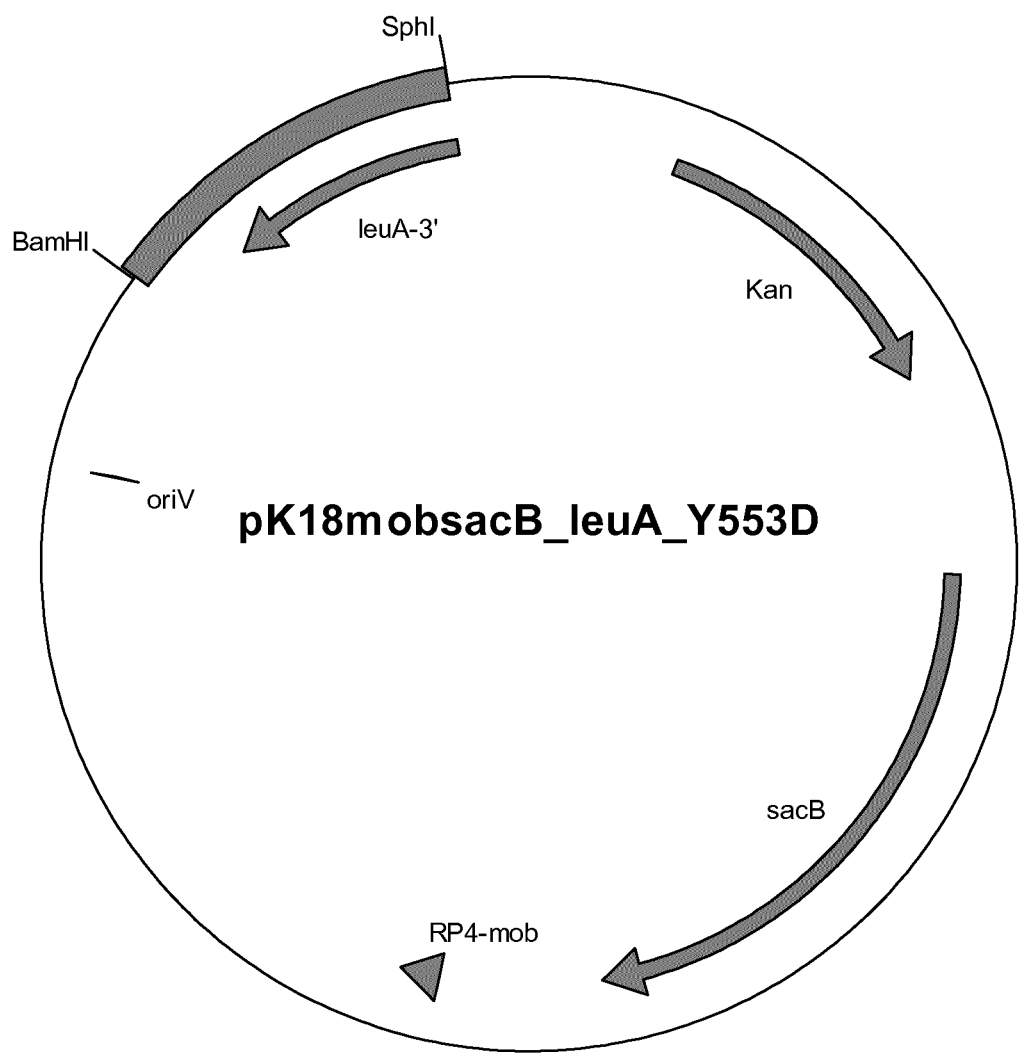

ical compounds, for example L-amino acids such as

SEQUENCE LISTING

<160> NUMBER OF SEQ ID NOS: 13

<210> SEQ ID NO 1
<211> LENGTH: 1851
<212> TYPE: DNA
<213> ORGANISM: Corynebacterium glutamicum
<220> FEATURE:
<221> NAME/KEY: CDS
<222> LOCATION: (1)..(1851)
<223> OTHER INFORMATION: leuA encoding region

<400> SEQUENCE: 1

```
atg tct cct aac gat gca ttc atc tcc gca cct gcc aag atc gaa acc      48
Met Ser Pro Asn Asp Ala Phe Ile Ser Ala Pro Ala Lys Ile Glu Thr
1               5                  10                 15 cca gtt ggg cct cgc aac gaa ggc cag cca gca tgg aat aag cag cgt      96
Pro Val Gly Pro Arg Asn Glu Gly Gln Pro Ala Trp Asn Lys Gln Arg
            20                  25                  30 ggc tcc tca atg cca gtt aac cgc tac atg cct ttc gag gtt gag gta     144
Gly Ser Ser Met Pro Val Asn Arg Tyr Met Pro Phe Glu Val Glu Val
        35                  40                  45 gaa gat att tct ctg ccg gac cgc act tgg cca gat aaa aaa atc acc     192
Glu Asp Ile Ser Leu Pro Asp Arg Thr Trp Pro Asp Lys Lys Ile Thr
50                  55                  60 gtt gca cct cag tgg tgt gct gtt gac ctg cgt gac ggc aac cag gct     240
Val Ala Pro Gln Trp Cys Ala Val Asp Leu Arg Asp Gly Asn Gln Ala
65                  70                  75                  80 ctg att gat ccg atg tct cct gag cgt aag cgc cgc atg ttt gag ctg     288
Leu Ile Asp Pro Met Ser Pro Glu Arg Lys Arg Arg Met Phe Glu Leu
                85                  90                  95 ctg gtt cag atg ggc ttc aaa gaa atc gag gtc ggt ttc cct tca gct     336
Leu Val Gln Met Gly Phe Lys Glu Ile Glu Val Gly Phe Pro Ser Ala
            100                 105                 110 tcc cag act gat ttt gat ttc gtt cgt gag atc atc gaa aag ggc atg     384
Ser Gln Thr Asp Phe Asp Phe Val Arg Glu Ile Ile Glu Lys Gly Met
        115                 120                 125 atc cct gac gat gtc acc att cag gtt ctg gtt cag gct cgt gag cac     432
Ile Pro Asp Asp Val Thr Ile Gln Val Leu Val Gln Ala Arg Glu His
130                 135                 140 ctg att cgc cgt act ttt gaa gct tgc gaa ggc gca aaa aac gtt atc     480
Leu Ile Arg Arg Thr Phe Glu Ala Cys Glu Gly Ala Lys Asn Val Ile
145                 150                 155                 160 gtg cac ttc tac aac tcc acc tcc atc ctg cag cgc aac gtg gtg ttc     528
Val His Phe Tyr Asn Ser Thr Ser Ile Leu Gln Arg Asn Val Val Phe
                165                 170                 175 cgc atg gac aag gtg cag gtg aag aag ctg gct acc gat gcc gct gaa     576
Arg Met Asp Lys Val Gln Val Lys Lys Leu Ala Thr Asp Ala Ala Glu
            180                 185                 190 cta atc aag acc atc gct cag gat tac cca gac acc aac tgg cgc tgg     624
Leu Ile Lys Thr Ile Ala Gln Asp Tyr Pro Asp Thr Asn Trp Arg Trp
        195                 200                 205 cag tac tcc cct gag tcc ttc acc ggc act gag gtt gag tac gcc aag     672
Gln Tyr Ser Pro Glu Ser Phe Thr Gly Thr Glu Val Glu Tyr Ala Lys
210                 215                 220 gaa gtt gtg gac gca gtt gtt gag gtc atg gat cca act cct gag aac     720
Glu Val Val Asp Ala Val Val Glu Val Met Asp Pro Thr Pro Glu Asn
225                 230                 235                 240 cca atg atc atc aac ctg cct tcc acc gtt gag atg atc acc cct aac     768
Pro Met Ile Ile Asn Leu Pro Ser Thr Val Glu Met Ile Thr Pro Asn
                245                 250                 255 gtt tac gca gac tcc att gaa tgg atg cac cgc aat cta aac cgt cgt     816
Val Tyr Ala Asp Ser Ile Glu Trp Met His Arg Asn Leu Asn Arg Arg
            260                 265                 270 gat tcc att atc ctg tcc ctg cac ccg cac aat gac cgt ggc acc ggc     864
Asp Ser Ile Ile Leu Ser Leu His Pro His Asn Asp Arg Gly Thr Gly
        275                 280                 285
```

-continued

| | |
|---|---|
| gtt ggc gca gct gag ctg ggc tac atg gct ggc gct gac cgc atc gaa<br>Val Gly Ala Ala Glu Leu Gly Tyr Met Ala Gly Ala Asp Arg Ile Glu<br>290                        295                     300 | 912 |
| ggc tgc ctg ttc ggc aac ggc gag cgc acc ggc aac gtc tgc ctg gtc<br>Gly Cys Leu Phe Gly Asn Gly Glu Arg Thr Gly Asn Val Cys Leu Val<br>305                     310                        315                 320 | 960 |
| acc ctg gca ctg aac atg ctg acc cag ggc gtt gac cct cag ctg gac<br>Thr Leu Ala Leu Asn Met Leu Thr Gln Gly Val Asp Pro Gln Leu Asp<br>                        325                        330                     335 | 1008 |
| ttc acc gat ata cgc cag atc cgc agc acc gtt gaa tac tgc aac cag<br>Phe Thr Asp Ile Arg Gln Ile Arg Ser Thr Val Glu Tyr Cys Asn Gln<br>                          340                        345                     350 | 1056 |
| ctg cgc gtt cct gag cgc cac cca tac ggc ggt gac ctg gtc ttc acc<br>Leu Arg Val Pro Glu Arg His Pro Tyr Gly Gly Asp Leu Val Phe Thr<br>            355                        360                        365 | 1104 |
| gct ttc tcc ggt tcc cac cag gac gct gtg aac aag ggt ctg gac gcc<br>Ala Phe Ser Gly Ser His Gln Asp Ala Val Asn Lys Gly Leu Asp Ala<br>370                        375                     380 | 1152 |
| atg gct gcc aag gtt cag cca ggt gct agc tcc act gaa gtt tct tgg<br>Met Ala Ala Lys Val Gln Pro Gly Ala Ser Ser Thr Glu Val Ser Trp<br>385                        390                        395                 400 | 1200 |
| gag cag ctg cgc gac acc gaa tgg gag gtt cct tac ctg cct atc gat<br>Glu Gln Leu Arg Asp Thr Glu Trp Glu Val Pro Tyr Leu Pro Ile Asp<br>                        405                        410                     415 | 1248 |
| cca aag gat gtc ggt cgc gac tac gag gct gtt atc cgc gtg aac tcc<br>Pro Lys Asp Val Gly Arg Asp Tyr Glu Ala Val Ile Arg Val Asn Ser<br>                      420                        425                   430 | 1296 |
| cag tcc ggc aag ggc ggt gtt gct tac atc atg aag acc gat cac ggt<br>Gln Ser Gly Lys Gly Gly Val Ala Tyr Ile Met Lys Thr Asp His Gly<br>                        435                        440                   445 | 1344 |
| ctg cag atc cct cgc tcc atg cag gtt gag ttc tcc acc gtt gtc cag<br>Leu Gln Ile Pro Arg Ser Met Gln Val Glu Phe Ser Thr Val Val Gln<br>            450                        455                        460 | 1392 |
| aac gtc acc gac gct gag ggc ggc gag gtc aac tcc aag gca atg tgg<br>Asn Val Thr Asp Ala Glu Gly Gly Glu Val Asn Ser Lys Ala Met Trp<br>465                        470                        475                 480 | 1440 |
| gat atc ttc gcc acc gag tac ctg gag cgc acc gca cca gtt gag cag<br>Asp Ile Phe Ala Thr Glu Tyr Leu Glu Arg Thr Ala Pro Val Glu Gln<br>                        485                        490                     495 | 1488 |
| atc gcg ctg cgc gtc gag aac gct cag acc gaa aac gag gat gca tcc<br>Ile Ala Leu Arg Val Glu Asn Ala Gln Thr Glu Asn Glu Asp Ala Ser<br>                      500                        505                   510 | 1536 |
| atc acc gcc gag ctc atc cac aac ggc aag gac gtc acc gtc gat ggc<br>Ile Thr Ala Glu Leu Ile His Asn Gly Lys Asp Val Thr Val Asp Gly<br>                 515                        520                     525 | 1584 |
| cgc ggc aac ggc cca ctg gcc gct tac gcc aac gcg ctg gag aag ctg<br>Arg Gly Asn Gly Pro Leu Ala Ala Tyr Ala Asn Ala Leu Glu Lys Leu<br>530                        535                     540 | 1632 |
| ggc atc gac gtt gag atc cag gaa tac aac cag cac gcc cgc acc tcg<br>Gly Ile Asp Val Glu Ile Gln Glu Tyr Asn Gln His Ala Arg Thr Ser<br>545                        550                        555                 560 | 1680 |
| ggc gac gat gca gaa gca gcc gcc tac gtg ctg gct gag gtc aac ggc<br>Gly Asp Asp Ala Glu Ala Ala Ala Tyr Val Leu Ala Glu Val Asn Gly<br>                        565                        570                   575 | 1728 |
| cgc aag gtc tgg ggc gtc ggc atc gct ggc tcc atc acc tac gct tcg<br>Arg Lys Val Trp Gly Val Gly Ile Ala Gly Ser Ile Thr Tyr Ala Ser<br>                 580                        585                     590 | 1776 |
| ctg aag gca gtg acc tcc gcc gta aac cgc gcg ctg gac gtc aac cac<br>Leu Lys Ala Val Thr Ser Ala Val Asn Arg Ala Leu Asp Val Asn His<br>            595                        600                     605 | 1824 |

```
gag gca gtc ctg gct ggc ggc gtt taa                              1851
Glu Ala Val Leu Ala Gly Gly Val
    610             615

<210> SEQ ID NO 2
<211> LENGTH: 616
<212> TYPE: PRT
<213> ORGANISM: Corynebacterium glutamicum
<220> FEATURE:
<221> NAME/KEY: misc_feature
<222> LOCATION: (553)..(553)
<223> OTHER INFORMATION: Xaa can be any proteinogenic amino acid except
      for Tyr

<400> SEQUENCE: 2

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Gly Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190

Leu Ile Lys Thr Ile Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
            260                 265                 270

Asp Ser Ile Ile Leu Ser Leu His Pro His Asn Asp Arg Gly Thr Gly
        275                 280                 285

Val Gly Ala Ala Glu Leu Gly Tyr Met Ala Gly Ala Asp Arg Ile Glu
    290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
```

```
            325                 330                 335
Phe Thr Asp Ile Arg Gln Ile Arg Ser Thr Val Glu Tyr Cys Asn Gln
        340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
        435                 440                 445

Leu Gln Ile Pro Arg Ser Met Gln Val Glu Phe Ser Thr Val Val Gln
        450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510

Ile Thr Ala Glu Leu Ile His Asn Gly Lys Asp Val Thr Val Asp Gly
        515                 520                 525

Arg Gly Asn Gly Pro Leu Ala Ala Tyr Ala Asn Ala Leu Glu Lys Leu
    530                 535                 540

Gly Ile Asp Val Glu Ile Gln Glu Xaa Asn Gln His Ala Arg Thr Ser
545                 550                 555                 560

Gly Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605

Glu Ala Val Leu Ala Gly Gly Val
        610                 615

<210> SEQ ID NO 3
<211> LENGTH: 3851
<212> TYPE: DNA
<213> ORGANISM: Corynebacterium glutamicum
<220> FEATURE:
<221> NAME/KEY: CDS
<222> LOCATION: (1001)..(2851)
<223> OTHER INFORMATION: leuA encoding region

<400> SEQUENCE: 3
cctttactca atgctctgat gacaccgatg tggtgggcag gcatgagtac cgcgatgctg      60
gcatatttct tacaaacagt agcacttggt ttcggcaccc tcttggtagt gcaaccagtg     120
cttgtcctgt cgctgatgtt cacgctgccg ctctcagcac gattcaatgg ctaccgacta     180
cgccgaactg aaatcttctg ggctacccte ctcaccgtag ccgtgggcat catgatcgtt     240
ttgggacgcc cccttcccgg aaaccccccac cccccactcg atcgatggat tccagtactt     300
ttagtcggcg ttgcagtaat gggtggaatg tggctgcttg cggaatacgt attaaagaag     360
```

-continued

```
gacaaagccc tcatccttgg tcttgtgacg ggtgcattgt ttggctacgt agcagtgatg     420
tccaaagccg cggtggatct ttttgtccat caaggcataa cgggactcat cttgaactgg     480
gaaggctacg gcctaatcct caccgcatta cttggaacaa tcgtgcagca gtattccttt     540
aacgctggcg aactacaaaa atcgctaccc gccatgacca ttgccgaacc aattgttgcc     600
ttcagtttgg gctacttggt tctgggcgaa aaattccaag tcgtggactg ggaatggatc     660
gccatgggca tcgcactact ggtgatgatt gtttccacca ttgcactgtc tcgtacaagc     720
acaatgccgg ccggatcgaa aaggtaaaac tccaaagttc ccccgagac atgacagcac      780 tggaactggg cgtcgaaaag ctttttaaa agaaaactcc cccgagttgc tacccacacc      840
acaaagttgt tgtatgcttc accacatgac ttcgcgtgcg aatctacttc ttcttcgccg     900
cggcgggtcc cagaggtctt aacacgaccg gcatcccgtc gcggagtttg tgttgccgg      960 tcgtggaccc acccaaaact ttttaagaag gttgaacaca atg tct cct aac gat      1015
                                              Met Ser Pro Asn Asp
                                              1               5 gca ttc atc tcc gca cct gcc aag atc gaa acc cca gtt ggg cct cgc      1063
Ala Phe Ile Ser Ala Pro Ala Lys Ile Glu Thr Pro Val Gly Pro Arg
         10                  15                  20 aac gaa ggc cag cca gca tgg aat aag cag cgt ggc tcc tca atg cca      1111
Asn Glu Gly Gln Pro Ala Trp Asn Lys Gln Arg Gly Ser Ser Met Pro
     25                  30                  35 gtt aac cgc tac atg cct ttc gag gtt gag gta gaa gat att tct ctg      1159
Val Asn Arg Tyr Met Pro Phe Glu Val Glu Val Glu Asp Ile Ser Leu
 40                  45                  50 ccg gac cgc act tgg cca gat aaa aaa atc acc gtt gca cct cag tgg      1207
Pro Asp Arg Thr Trp Pro Asp Lys Lys Ile Thr Val Ala Pro Gln Trp
 55                  60                  65 tgt gct gtt gac ctg cgt gac ggc aac cag gct ctg att gat ccg atg      1255
Cys Ala Val Asp Leu Arg Asp Gly Asn Gln Ala Leu Ile Asp Pro Met
70                  75                  80                  85 tct cct gag cgt aag cgc cgc atg ttt gag ctg ctg gtt cag atg ggc      1303
Ser Pro Glu Arg Lys Arg Arg Met Phe Glu Leu Leu Val Gln Met Gly
             90                  95                 100 ttc aaa gaa atc gag gtc ggt ttc cct tca gct tcc cag act gat ttt      1351
Phe Lys Glu Ile Glu Val Gly Phe Pro Ser Ala Ser Gln Thr Asp Phe
         105                 110                 115 gat ttc gtt cgt gag atc atc gaa aag ggc atg atc cct gac gat gtc      1399
Asp Phe Val Arg Glu Ile Ile Glu Lys Gly Met Ile Pro Asp Asp Val
     120                 125                 130 acc att cag gtt ctg gtt cag gct cgt gag cac ctg att cgc cgt act      1447
Thr Ile Gln Val Leu Val Gln Ala Arg Glu His Leu Ile Arg Arg Thr
 135                 140                 145 ttt gaa gct tgc gaa ggc gca aaa aac gtt atc gtg cac ttc tac aac      1495
Phe Glu Ala Cys Glu Gly Ala Lys Asn Val Ile Val His Phe Tyr Asn
150                 155                 160                 165 tcc acc tcc atc ctg cag cgc aac gtg gtg ttc cgc atg gac aag gtg      1543
Ser Thr Ser Ile Leu Gln Arg Asn Val Val Phe Arg Met Asp Lys Val
             170                 175                 180 cag gtg aag aag ctg gct acc gat gcc gct gaa cta atc aag acc atc      1591
Gln Val Lys Lys Leu Ala Thr Asp Ala Ala Glu Leu Ile Lys Thr Ile
         185                 190                 195 gct cag gat tac cca gac acc aac tgg cgc tgg cag tac tcc cct gag      1639
Ala Gln Asp Tyr Pro Asp Thr Asn Trp Arg Trp Gln Tyr Ser Pro Glu
     200                 205                 210 tcc ttc acc ggc act gag gtt gag tac gcc aag gaa gtt gtg gac gca      1687
Ser Phe Thr Gly Thr Glu Val Glu Tyr Ala Lys Glu Val Val Asp Ala
```

-continued

```
            215                 220                 225
gtt gtt gag gtc atg gat cca act cct gag aac cca atg atc atc aac   1735
Val Val Glu Val Met Asp Pro Thr Pro Glu Asn Pro Met Ile Ile Asn
230                 235                 240                 245 ctg cct tcc acc gtt gag atg atc acc cct aac gtt tac gca gac tcc   1783
Leu Pro Ser Thr Val Glu Met Ile Thr Pro Asn Val Tyr Ala Asp Ser
                250                 255                 260 att gaa tgg atg cac cgc aat cta aac cgt cgt gat tcc att atc ctg   1831
Ile Glu Trp Met His Arg Asn Leu Asn Arg Arg Asp Ser Ile Ile Leu
            265                 270                 275 tcc ctg cac ccg cac aat gac cgt ggc acc ggc gtt ggc gca gct gag   1879
Ser Leu His Pro His Asn Asp Arg Gly Thr Gly Val Gly Ala Ala Glu
        280                 285                 290 ctg ggc tac atg gct ggc gct gac cgc atc gaa ggc tgc ctg ttc ggc   1927
Leu Gly Tyr Met Ala Gly Ala Asp Arg Ile Glu Gly Cys Leu Phe Gly
    295                 300                 305 aac ggc gag cgc acc ggc aac gtc tgc ctg gtc acc ctg gca ctg aac   1975
Asn Gly Glu Arg Thr Gly Asn Val Cys Leu Val Thr Leu Ala Leu Asn
310                 315                 320                 325 atg ctg acc cag ggc gtt gac cct cag ctg gac ttc acc gat ata cgc   2023
Met Leu Thr Gln Gly Val Asp Pro Gln Leu Asp Phe Thr Asp Ile Arg
                330                 335                 340 cag atc cgc agc acc gtt gaa tac tgc aac cag ctg cgc gtt cct gag   2071
Gln Ile Arg Ser Thr Val Glu Tyr Cys Asn Gln Leu Arg Val Pro Glu
            345                 350                 355 cgc cac cca tac ggc ggt gac ctg gtc ttc acc gct ttc tcc ggt tcc   2119
Arg His Pro Tyr Gly Gly Asp Leu Val Phe Thr Ala Phe Ser Gly Ser
        360                 365                 370 cac cag gac gct gtg aac aag ggt ctg gac gcc atg gct gcc aag gtt   2167
His Gln Asp Ala Val Asn Lys Gly Leu Asp Ala Met Ala Ala Lys Val
    375                 380                 385 cag cca ggt gct agc tcc act gaa gtt tct tgg gag cag ctg cgc gac   2215
Gln Pro Gly Ala Ser Ser Thr Glu Val Ser Trp Glu Gln Leu Arg Asp
390                 395                 400                 405 acc gaa tgg gag gtt cct tac ctg cct atc gat cca aag gat gtc ggt   2263
Thr Glu Trp Glu Val Pro Tyr Leu Pro Ile Asp Pro Lys Asp Val Gly
                410                 415                 420 cgc gac tac gag gct gtt atc cgc gtg aac tcc cag tcc ggc aag ggc   2311
Arg Asp Tyr Glu Ala Val Ile Arg Val Asn Ser Gln Ser Gly Lys Gly
            425                 430                 435 ggc gtt gct tac atc atg aag acc gat cac ggt ctg cag atc cct cgc   2359
Gly Val Ala Tyr Ile Met Lys Thr Asp His Gly Leu Gln Ile Pro Arg
        440                 445                 450 tcc atg cag gtt gag ttc tcc acc gtt gtc cag aac gtc acc gac gct   2407
Ser Met Gln Val Glu Phe Ser Thr Val Val Gln Asn Val Thr Asp Ala
    455                 460                 465 gag ggc ggc gag gtc aac tcc aag gca atg tgg gat atc ttc gcc acc   2455
Glu Gly Gly Glu Val Asn Ser Lys Ala Met Trp Asp Ile Phe Ala Thr
470                 475                 480                 485 gag tac ctg gag cgc acc gca cca gtt gag cag atc gcg ctg cgc gtc   2503
Glu Tyr Leu Glu Arg Thr Ala Pro Val Glu Gln Ile Ala Leu Arg Val
                490                 495                 500 gag aac gct cag acc gaa aac gag gat gca tcc atc acc gcc gag ctc   2551
Glu Asn Ala Gln Thr Glu Asn Glu Asp Ala Ser Ile Thr Ala Glu Leu
            505                 510                 515 atc cac aac ggc aag gac gtc acc gtc gat ggc cgc ggc aac ggc cca   2599
Ile His Asn Gly Lys Asp Val Thr Val Asp Gly Arg Gly Asn Gly Pro
        520                 525                 530 ctg gcc gct tac gcc aac gcg ctg gag aag ctg ggc atc gac gtt gag   2647
Leu Ala Ala Tyr Ala Asn Ala Leu Glu Lys Leu Gly Ile Asp Val Glu
```

```
Leu Ala Ala Tyr Ala Asn Ala Leu Glu Lys Leu Gly Ile Asp Val Glu
            535                 540                 545 atc cag gaa tac aac cag cac gcc cgc acc tcg ggc gac gat gca gaa      2695
Ile Gln Glu Tyr Asn Gln His Ala Arg Thr Ser Gly Asp Asp Ala Glu
550                 555                 560                 565 gca gcc gcc tac gtg ctg gct gag gtc aac ggc cgc aag gtc tgg ggc      2743
Ala Ala Ala Tyr Val Leu Ala Glu Val Asn Gly Arg Lys Val Trp Gly
                570                 575                 580 gtc ggc atc gct ggc tcc atc acc tac gct tcg ctg aag gca gtg acc      2791
Val Gly Ile Ala Gly Ser Ile Thr Tyr Ala Ser Leu Lys Ala Val Thr
            585                 590                 595 tcc gcc gta aac cgc gcg ctg gac gtc aac cac gag gca gtc ctg gct      2839
Ser Ala Val Asn Arg Ala Leu Asp Val Asn His Glu Ala Val Leu Ala
        600                 605                 610 ggc ggc gtt taa gctttacgac gcctccccct aggctctaca aaccggtggc          2891
Gly Gly Val
    615 aagaattcca cgatgttgaa aattcttgcc accggtttcg tgggtgatag gaatatagag    2951
cctgtttcat gcctcgagtt ttctcaaatg attttttcgta tgcccaaggc cctcaaaacc   3011
cattagaagc acctctgggg gatataacct acccaggcca aagtcgaaat ttgagagcga    3071
ccaaaccatg agacccaaaa acttgaaaaa acatgctttc tggggcctta tgtctggtac    3131
caacgagtcc cggcgctttt cacccattag attgcgcaag ctgggcgtgc aaccatcagt    3191
ttttaaacct ttcttcacca ggtgatcgaa aatgcccggg tatcctatgg atttggtcat    3251
ctacaaccat caacgaccat ttgcatgcct tgaaatgctg tgaaacctct ctaagcaact    3311
agagttgtaa aaatgagcac cacttcggaa tcacaagatc acgccgcaag aatcgaagct    3371
gagcgccaag aagctattga gcggctcct tttgtttccg tcagcattca atcaagtgga     3431
atccacccat cgacttcacg catggtcacc attgatttgg taacgctgtc ccctaatttg    3491
gagccggtgg aaacttttca tgccgtgttg gattccaaaa ctgatcctgg cccttccac     3551
cttcatggcg tgacagagga agaatttgcc agcgctaagc gtttcggcca gattttgaaa    3611
agcttggacc gcctcatcga tggtcgtacc ctgttgatcc acaatgctgc gcgaagttgg    3671
ggctttattg ttttccgaagc caagcgcgct atgaatgatg ctgcgcgcgc caatcgcaac    3731
agcaatcgtg gaaatcgccg tggtggtcgc ggacgccgca ggcagcgcgt ggggcacatc    3791
ccaaagccgc tggtgatcgt cgatacgctt gcatcggcgc gtcgacaagc aatcgcttta    3851
```

<210> SEQ ID NO 4
<211> LENGTH: 616
<212> TYPE: PRT
<213> ORGANISM: Corynebacterium glutamicum

<400> SEQUENCE: 4

```
Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65              70                  75                  80

Leu Ile Asp Pro Met Ser Pro Glu Arg Lys Arg Arg Met Phe Glu Leu
```

```
            85                  90                  95
Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Gly Met
            115                 120                 125

Ile Pro Asp Asp Val Thr Ile Gln Val Leu Val Gln Ala Arg Glu His
            130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
                180                 185                 190

Leu Ile Lys Thr Ile Ala Gln Asp Tyr Pro Asp Thr Asn Trp Arg Trp
                195                 200                 205

Gln Tyr Ser Pro Glu Ser Phe Thr Gly Thr Glu Val Glu Tyr Ala Lys
            210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
                275                 280                 285

Val Gly Ala Ala Glu Leu Gly Tyr Met Ala Gly Ala Asp Arg Ile Glu
            290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
            355                 360                 365

Ala Phe Ser Gly Ser His Gln Asp Ala Val Asn Lys Gly Leu Asp Ala
            370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
            420                 425                 430

Gln Ser Gly Lys Gly Gly Val Ala Tyr Ile Met Lys Thr Asp His Gly
            435                 440                 445

Leu Gln Ile Pro Arg Ser Met Gln Val Glu Phe Ser Thr Val Val Gln
            450                 455                 460

Asn Val Thr Asp Ala Glu Gly Gly Glu Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
            500                 505                 510
```

-continued

```
Ile Thr Ala Glu Leu Ile His Asn Gly Lys Asp Val Thr Val Asp Gly
        515                 520                 525
Arg Gly Asn Gly Pro Leu Ala Ala Tyr Ala Asn Ala Leu Glu Lys Leu
    530                 535                 540
Gly Ile Asp Val Glu Ile Gln Glu Tyr Asn Gln His Ala Arg Thr Ser
545                 550                 555                 560
Gly Asp Asp Ala Glu Ala Ala Tyr Val Leu Ala Glu Val Asn Gly
                565                 570                 575
Arg Lys Val Trp Gly Val Gly Ile Ala Gly Ser Ile Thr Tyr Ala Ser
                580                 585                 590
Leu Lys Ala Val Thr Ser Ala Val Asn Arg Ala Leu Asp Val Asn His
        595                 600                 605
Glu Ala Val Leu Ala Gly Gly Val
        610                 615
```

<210> SEQ ID NO 5
<211> LENGTH: 1851
<212> TYPE: DNA
<213> ORGANISM: Corynebacterium glutamicum
<220> FEATURE:
<221> NAME/KEY: CDS
<222> LOCATION: (1)..(1851)
<223> OTHER INFORMATION: leuA encoding region
<220> FEATURE:
<221> NAME/KEY: mutation
<222> LOCATION: (1657)..(1657)
<223> OTHER INFORMATION: Exchange of t for g

<400> SEQUENCE: 5

```
atg tct cct aac gat gca ttc atc tcc gca cct gcc aag atc gaa acc      48
Met Ser Pro Asn Asp Ala Phe Ile Ser Ala Pro Ala Lys Ile Glu Thr
1               5                   10                  15 cca gtt ggg cct cgc aac gaa ggc cag cca gca tgg aat aag cag cgt      96
Pro Val Gly Pro Arg Asn Glu Gly Gln Pro Ala Trp Asn Lys Gln Arg
            20                  25                  30 ggc tcc tca atg cca gtt aac cgc tac atg cct ttc gag gtt gag gta     144
Gly Ser Ser Met Pro Val Asn Arg Tyr Met Pro Phe Glu Val Glu Val
        35                  40                  45 gaa gat att tct ctg ccg gac cgc act tgg cca gat aaa aaa atc acc     192
Glu Asp Ile Ser Leu Pro Asp Arg Thr Trp Pro Asp Lys Lys Ile Thr
    50                  55                  60 gtt gca cct cag tgg tgt gct gtt gac ctg cgt gac ggc aac cag gct     240
Val Ala Pro Gln Trp Cys Ala Val Asp Leu Arg Asp Gly Asn Gln Ala
65                  70                  75                  80 ctg att gat ccg atg tct cct gag cgt aag cgc cgc atg ttt gag ctg     288
Leu Ile Asp Pro Met Ser Pro Glu Arg Lys Arg Arg Met Phe Glu Leu
                85                  90                  95 ctg gtt cag atg ggc ttc aaa gaa atc gag gtc ggt ttc cct tca gct     336
Leu Val Gln Met Gly Phe Lys Glu Ile Glu Val Gly Phe Pro Ser Ala
            100                 105                 110 tcc cag act gat ttt gat ttc gtt cgt gag atc atc gaa aag ggc atg     384
Ser Gln Thr Asp Phe Asp Phe Val Arg Glu Ile Ile Glu Lys Gly Met
        115                 120                 125 atc cct gac gat gtc acc att cag gtt ctg gtt cag gct cgt gag cac     432
Ile Pro Asp Asp Val Thr Ile Gln Val Leu Val Gln Ala Arg Glu His
    130                 135                 140 ctg att cgc cgt act ttt gaa gct tgc gaa ggc gca aaa aac gtt atc     480
Leu Ile Arg Arg Thr Phe Glu Ala Cys Glu Gly Ala Lys Asn Val Ile
145                 150                 155                 160 gtg cac ttc tac aac tcc acc tcc atc ctg cag cgc aac gtg gtg ttc     528
```

```
                Val His Phe Tyr Asn Ser Thr Ser Ile Leu Gln Arg Asn Val Val Phe
                                165                 170                 175 cgc atg gac aag gtg cag gtg aag aag ctg gct acc gat gcc gct gaa        576
Arg Met Asp Lys Val Gln Val Lys Lys Leu Ala Thr Asp Ala Ala Glu
            180                 185                 190 cta atc aag acc atc gct cag gat tac cca gac acc aac tgg cgc tgg        624
Leu Ile Lys Thr Ile Ala Gln Asp Tyr Pro Asp Thr Asn Trp Arg Trp
195                 200                 205 cag tac tcc cct gag tcc ttc acc ggc act gag gtt gag tac gcc aag        672
Gln Tyr Ser Pro Glu Ser Phe Thr Gly Thr Glu Val Glu Tyr Ala Lys
    210                 215                 220 gaa gtt gtg gac gca gtt gtt gag gtc atg gat cca act cct gag aac        720
Glu Val Val Asp Ala Val Val Glu Val Met Asp Pro Thr Pro Glu Asn
225                 230                 235                 240 cca atg atc atc aac ctg cct tcc acc gtt gag atg atc acc cct aac        768
Pro Met Ile Ile Asn Leu Pro Ser Thr Val Glu Met Ile Thr Pro Asn
                245                 250                 255 gtt tac gca gac tcc att gaa tgg atg cac cgc aat cta aac cgt cgt        816
Val Tyr Ala Asp Ser Ile Glu Trp Met His Arg Asn Leu Asn Arg Arg
                260                 265                 270 gat tcc att atc ctg tcc ctg cac ccg cac aat gac cgt ggc acc ggc        864
Asp Ser Ile Ile Leu Ser Leu His Pro His Asn Asp Arg Gly Thr Gly
            275                 280                 285 gtt ggc gca gct gag ctg ggc tac atg gct ggc gct gac cgc atc gaa        912
Val Gly Ala Ala Glu Leu Gly Tyr Met Ala Gly Ala Asp Arg Ile Glu
290                 295                 300 ggc tgc ctg ttc ggc aac ggc gag cgc acc ggc aac gtc tgc ctg gtc        960
Gly Cys Leu Phe Gly Asn Gly Glu Arg Thr Gly Asn Val Cys Leu Val
305                 310                 315                 320 acc ctg gca ctg aac atg ctg acc cag ggc gtt gac cct cag ctg gac       1008
Thr Leu Ala Leu Asn Met Leu Thr Gln Gly Val Asp Pro Gln Leu Asp
                325                 330                 335 ttc acc gat ata cgc cag atc cgc agc acc gtt gaa tac tgc aac cag       1056
Phe Thr Asp Ile Arg Gln Ile Arg Ser Thr Val Glu Tyr Cys Asn Gln
                340                 345                 350 ctg cgc gtt cct gag cgc cac cca tac ggc ggt gac ctg gtc ttc acc       1104
Leu Arg Val Pro Glu Arg His Pro Tyr Gly Gly Asp Leu Val Phe Thr
            355                 360                 365 gct ttc tcc ggt tcc cac cag gac gct gtg aac aag ggt ctg gac gcc       1152
Ala Phe Ser Gly Ser His Gln Asp Ala Val Asn Lys Gly Leu Asp Ala
370                 375                 380 atg gct gcc aag gtt cag cca ggt gct agc tcc act gaa gtt tct tgg       1200
Met Ala Ala Lys Val Gln Pro Gly Ala Ser Ser Thr Glu Val Ser Trp
385                 390                 395                 400 gag cag ctg cgc gac acc gaa tgg gag gtt cct tac ctg cct atc gat       1248
Glu Gln Leu Arg Asp Thr Glu Trp Glu Val Pro Tyr Leu Pro Ile Asp
                405                 410                 415 cca aag gat gtc ggt cgc gac tac gag gct gtt atc cgc gtg aac tcc       1296
Pro Lys Asp Val Gly Arg Asp Tyr Glu Ala Val Ile Arg Val Asn Ser
                420                 425                 430 cag tcc ggc aag ggc ggc gtt gct tac atc atg aag acc gat cac ggt       1344
Gln Ser Gly Lys Gly Gly Val Ala Tyr Ile Met Lys Thr Asp His Gly
            435                 440                 445 ctg cag atc cct cgc tcc atg cag gtt gag ttc tcc acc gtt gtc cag       1392
Leu Gln Ile Pro Arg Ser Met Gln Val Glu Phe Ser Thr Val Val Gln
450                 455                 460 aac gtc acc gac gct gag ggc ggc gag gtc aac tcc aag gca atg tgg       1440
Asn Val Thr Asp Ala Glu Gly Gly Glu Val Asn Ser Lys Ala Met Trp
465                 470                 475                 480
```

```
gat atc ttc gcc acc gag tac ctg gag cgc acc gca cca gtt gag cag    1488
Asp Ile Phe Ala Thr Glu Tyr Leu Glu Arg Thr Ala Pro Val Glu Gln
                485                 490                 495 atc gcg ctg cgc gtc gag aac gct cag acc gaa aac gag gat gca tcc    1536
Ile Ala Leu Arg Val Glu Asn Ala Gln Thr Glu Asn Glu Asp Ala Ser
        500                 505                 510 atc acc gcc gag ctc atc cac aac ggc aag gac gtc acc gtc gat ggc    1584
Ile Thr Ala Glu Leu Ile His Asn Gly Lys Asp Val Thr Val Asp Gly
    515                 520                 525 cgc ggc aac ggc cca ctg gcc gct tac gcc aac gcg ctg gag aag ctg    1632
Arg Gly Asn Gly Pro Leu Ala Ala Tyr Ala Asn Ala Leu Glu Lys Leu
530                 535                 540 ggc atc gac gtt gag atc cag gaa gac aac cag cac gcc cgc acc tcg    1680
Gly Ile Asp Val Glu Ile Gln Glu Asp Asn Gln His Ala Arg Thr Ser
545                 550                 555                 560 ggc gac gat gca gaa gca gcc gcc tac gtg ctg gct gag gtc aac ggc    1728
Gly Asp Asp Ala Glu Ala Ala Ala Tyr Val Leu Ala Glu Val Asn Gly
            565                 570                 575 cgc aag gtc tgg ggc gtc ggc atc gct ggc tcc atc acc tac gct tcg    1776
Arg Lys Val Trp Gly Val Gly Ile Ala Gly Ser Ile Thr Tyr Ala Ser
        580                 585                 590 ctg aag gca gtg acc tcc gcc gta aac cgc gcg ctg gac gtc aac cac    1824
Leu Lys Ala Val Thr Ser Ala Val Asn Arg Ala Leu Asp Val Asn His
    595                 600                 605 gag gca gtc ctg gct ggc ggc gtt taa                                 1851
Glu Ala Val Leu Ala Gly Gly Val
610                 615

<210> SEQ ID NO 6
<211> LENGTH: 616
<212> TYPE: PRT
<213> ORGANISM: Corynebacterium glutamicum

<400> SEQUENCE: 6

Met Ser Pro Asn Asp Ala Phe Ile Ser Ala Pro Ala Lys Ile Glu Thr
1               5                   10                  15

Pro Val Gly Pro Arg Asn Glu Gly Gln Pro Ala Trp Asn Lys Gln Arg
            20                  25                  30

Gly Ser Ser Met Pro Val Asn Arg Tyr Met Pro Phe Glu Val Glu Val
        35                  40                  45

Glu Asp Ile Ser Leu Pro Asp Arg Thr Trp Pro Asp Lys Lys Ile Thr
    50                  55                  60

Val Ala Pro Gln Trp Cys Ala Val Asp Leu Arg Asp Gly Asn Gln Ala
65                  70                  75                  80

Leu Ile Asp Pro Met Ser Pro Glu Arg Lys Arg Arg Met Phe Glu Leu
                85                  90                  95

Leu Val Gln Met Gly Phe Lys Glu Ile Glu Val Gly Phe Pro Ser Ala
            100                 105                 110

Ser Gln Thr Asp Phe Asp Phe Val Arg Glu Ile Ile Glu Lys Gly Met
        115                 120                 125

Ile Pro Asp Asp Val Thr Ile Gln Val Leu Val Gln Ala Arg Glu His
    130                 135                 140

Leu Ile Arg Arg Thr Phe Glu Ala Cys Glu Gly Ala Lys Asn Val Ile
145                 150                 155                 160

Val His Phe Tyr Asn Ser Thr Ser Ile Leu Gln Arg Asn Val Val Phe
                165                 170                 175

Arg Met Asp Lys Val Gln Val Lys Lys Leu Ala Thr Asp Ala Ala Glu
            180                 185                 190
```

```
Leu Ile Lys Thr Ile Ala Gln Asp Tyr Pro Asp Thr Asn Trp Arg Trp
        195                 200                 205

Gln Tyr Ser Pro Glu Ser Phe Thr Gly Thr Glu Val Glu Tyr Ala Lys
    210                 215                 220

Glu Val Val Asp Ala Val Val Glu Val Met Asp Pro Thr Pro Glu Asn
225                 230                 235                 240

Pro Met Ile Ile Asn Leu Pro Ser Thr Val Glu Met Ile Thr Pro Asn
                245                 250                 255

Val Tyr Ala Asp Ser Ile Glu Trp Met His Arg Asn Leu Asn Arg Arg
                260                 265                 270

Asp Ser Ile Ile Leu Ser Leu His Pro His Asn Asp Arg Gly Thr Gly
            275                 280                 285

Val Gly Ala Ala Glu Leu Gly Tyr Met Ala Gly Ala Asp Arg Ile Glu
        290                 295                 300

Gly Cys Leu Phe Gly Asn Gly Glu Arg Thr Gly Asn Val Cys Leu Val
305                 310                 315                 320

Thr Leu Ala Leu Asn Met Leu Thr Gln Gly Val Asp Pro Gln Leu Asp
                325                 330                 335

Phe Thr Asp Ile Arg Gln Ile Arg Ser Thr Val Glu Tyr Cys Asn Gln
                340                 345                 350

Leu Arg Val Pro Glu Arg His Pro Tyr Gly Gly Asp Leu Val Phe Thr
        355                 360                 365

Ala Phe Ser Gly Ser His Gln Asp Ala Val Asn Lys Gly Leu Asp Ala
        370                 375                 380

Met Ala Ala Lys Val Gln Pro Gly Ala Ser Ser Thr Glu Val Ser Trp
385                 390                 395                 400

Glu Gln Leu Arg Asp Thr Glu Trp Glu Val Pro Tyr Leu Pro Ile Asp
                405                 410                 415

Pro Lys Asp Val Gly Arg Asp Tyr Glu Ala Val Ile Arg Val Asn Ser
                420                 425                 430

Gln Ser Gly Lys Gly Val Ala Tyr Ile Met Lys Thr Asp His Gly
        435                 440                 445

Leu Gln Ile Pro Arg Ser Met Gln Val Glu Phe Ser Thr Val Val Gln
    450                 455                 460

Asn Val Thr Asp Ala Glu Gly Gly Val Asn Ser Lys Ala Met Trp
465                 470                 475                 480

Asp Ile Phe Ala Thr Glu Tyr Leu Glu Arg Thr Ala Pro Val Glu Gln
                485                 490                 495

Ile Ala Leu Arg Val Glu Asn Ala Gln Thr Glu Asn Glu Asp Ala Ser
                500                 505                 510

Ile Thr Ala Glu Leu Ile His Asn Gly Lys Asp Val Thr Val Asp Gly
            515                 520                 525

Arg Gly Asn Gly Pro Leu Ala Ala Tyr Ala Asn Ala Leu Glu Lys Leu
    530                 535                 540

Gly Ile Asp Val Glu Ile Gln Glu Asp Asn Gln His Ala Arg Thr Ser
545                 550                 555                 560

Gly Asp Asp Ala Glu Ala Ala Tyr Val Leu Ala Glu Val Asn Gly
                565                 570                 575

Arg Lys Val Trp Gly Val Gly Ile Ala Gly Ser Ile Thr Tyr Ala Ser
            580                 585                 590

Leu Lys Ala Val Thr Ser Ala Val Asn Arg Ala Leu Asp Val Asn His
        595                 600                 605
```

```
Glu Ala Val Leu Ala Gly Gly Val
    610             615
```

<210> SEQ ID NO 7
<211> LENGTH: 812
<212> TYPE: DNA
<213> ORGANISM: Corynebacterium glutamicum
<220> FEATURE:
<221> NAME/KEY: misc_feature
<222> LOCATION: (1)..(6)
<223> OTHER INFORMATION: SphI cutting site
<220> FEATURE:
<221> NAME/KEY: gene
<222> LOCATION: (7)..(600)
<223> OTHER INFORMATION: C terminus of the leuA gene
<220> FEATURE:
<221> NAME/KEY: mutation
<222> LOCATION: (406)..(406)
<223> OTHER INFORMATION: Exchange of t for g
<220> FEATURE:
<221> NAME/KEY: misc_feature
<222> LOCATION: (807)..(812)
<223> OTHER INFORMATION: BamH cutting site

<400> SEQUENCE: 7

```
gcatgcgtcg gtcgcgacta cgaggctgtt atccgcgtga actcccagtc cggcaagggc      60
ggcgttgctt acatcatgaa gaccgatcac ggtctgcaga tccctcgctc catgcaggtt     120
gagttctcca ccgttgtcca gaacgtcacc gacgctgagg gcggcgaggt caactccaag     180
gcaatgtggg atatcttcgc caccgagtac ctggagcgca ccgcaccagt tgagcagatc     240
gcgctgcgcg tcgagaacgc tcagaccgaa aacgaggatg catccatcac cgccgagctc     300
atccacaacg gcaaggacgt caccgtcgat ggccgcggca acgcccact ggccgcttac     360 gccaacgcgc tggagaagct gggcatcgac gttgagatcc aggaagacaa ccagcacgcc     420
cgcacctcgg gcgacgatgc agaagcagcc gcctacgtgc tggctgaggt caacggccgc     480
aaggtctggg gcgtcggcat cgctggctcc atcacctacg cttcgctgaa ggcagtgacc     540
tccgccgtaa accgcgcgct ggacgtcaac cacgaggcag tcctggctgg cggcgtttaa     600
gctttacgac gcctcccct aggctctaca aaccggtggc aagaattcca cgatgttgaa     660
aattcttgcc accggtttcg tgggtgatag gaatatagag cctgtttcat gcctcgagtt     720
ttctcaaatg attttttcgta tgcccaaggc cctcaaaacc cattagaagc acctctgggg     780
gatataacct acccaggcca aagtcgggat cc                                  812
```

<210> SEQ ID NO 8
<211> LENGTH: 30
<212> TYPE: DNA
<213> ORGANISM: Corynebacterium glutamicum
<220> FEATURE:
<221> NAME/KEY: misc_feature
<222> LOCATION: (1)..(30)
<223> OTHER INFORMATION: Primer ilvE-XbaI-fw

<400> SEQUENCE: 8

```
gctctagagc caagcctagc cattcctcaa                                       30
```

<210> SEQ ID NO 9
<211> LENGTH: 30
<212> TYPE: DNA
<213> ORGANISM: Corynebacterium glutamicum
<220> FEATURE:
<221> NAME/KEY: misc_feature
<222> LOCATION: (1)..(30)
<223> OTHER INFORMATION: Primer ilvE-XbaI-rev

```
<400> SEQUENCE: 9
gctctagagc cagccactgc attctcctta                                          30

<210> SEQ ID NO 10
<211> LENGTH: 32
<212> TYPE: DNA
<213> ORGANISM: Corynebacterium glutamicum
<220> FEATURE:
<221> NAME/KEY: misc_feature
<222> LOCATION: (1)..(32)
<223> OTHER INFORMATION: Primer leuA1

<400> SEQUENCE: 10
gatctatcta gattgagggc cttgggcata cg                                       32

<210> SEQ ID NO 11
<211> LENGTH: 32
<212> TYPE: DNA
<213> ORGANISM: Corynebacterium glutamicum
<220> FEATURE:
<221> NAME/KEY: misc_feature
<222> LOCATION: (1)..(32)
<223> OTHER INFORMATION: Primer leuA-2

<400> SEQUENCE: 11
gatctaggat ccgcgactac gaggctgtta tc                                       32

<210> SEQ ID NO 12
<211> LENGTH: 32
<212> TYPE: DNA
<213> ORGANISM: Corynebacterium glutamicum
<220> FEATURE:
<221> NAME/KEY: misc_feature
<222> LOCATION: (1)..(32)
<223> OTHER INFORMATION: Primer leuA-3

<400> SEQUENCE: 12
gatctatcta gaaagcttaa acgccgccag cc                                       32

<210> SEQ ID NO 13
<211> LENGTH: 6504
<212> TYPE: DNA
<213> ORGANISM: Corynebacterium glutamicum
<220> FEATURE:
<221> NAME/KEY: gene
<222> LOCATION: (365)..(1159)
<223> OTHER INFORMATION: kanamycin resistance gene
<220> FEATURE:
<221> NAME/KEY: gene
<222> LOCATION: (1651)..(3072)
<223> OTHER INFORMATION: sacB gene encoding the protein levansucrase
<220> FEATURE:
<221> NAME/KEY: misc_feature
<222> LOCATION: (3473)..(3571)
<223> OTHER INFORMATION: RP4 mobilization site
<220> FEATURE:
<221> NAME/KEY: rep_origin
<222> LOCATION: (5091)..(5093)
<223> OTHER INFORMATION: ColE1-like origin from pMB1
<220> FEATURE:
<221> NAME/KEY: misc_feature
<222> LOCATION: (5531)..(6330)
<223> OTHER INFORMATION: gene type fragment
<220> FEATURE:
<221> NAME/KEY: misc_feature
<222> LOCATION: (5737)..(6330)
<223> OTHER INFORMATION: C terminus of the leuA gene (594 bp)
<220> FEATURE:
<221> NAME/KEY: mutation
<222> LOCATION: (5929)..(5931)
<223> OTHER INFORMATION: T to G, changes the wild-type codon TAC
```

(encoding the amino acid Y, tyrosine) to the codon GAC (encoding
the amino acid D, aspartate) (Y553D)

<400> SEQUENCE: 13

```
cgataagcta gcttcacgct gccgcaagca ctcagggcgc aagggctgct aaaggaagcg      60
gaacacgtag aaagccagtc cgcagaaacg gtgctgaccc cggatgaatg tcagctactg     120
ggctatctgg acaagggaaa acgcaagcgc aaagagaaag caggtagctt gcagtgggct     180
tacatggcga tagctagact gggcggtttt atggacagca agcgaaccgg aattgccagc     240
tggggcgccc tctggtaagg ttgggaagcc ctgcaaagta aactggatgg ctttcttgcc     300
gccaaggatc tgatggcgca ggggatcaag atctgatcaa gagacaggat gaggatcgtt     360
tcgcatgatt gaacaagatg gattgcacgc aggttctccg gccgcttggg tggagaggct     420
attcggctat gactgggcac aacagacaat cggctgctct gatgccgccg tgttccggct     480
gtcagcgcag gggcgcccgg ttcttttttgt caagaccgac ctgtccggtg ccctgaatga     540
actccaagac gaggcagcgc ggctatcgtg gctggccacg acgggcgttc cttgcgcagc     600
tgtgctcgac gttgtcactg aagcgggaag ggactggctg ctattgggcg aagtgccggg     660
gcaggatctc ctgtcatctc accttgctcc tgccgagaaa gtatccatca tggctgatgc     720
aatgcggcgg ctgcatacgc ttgatccggc tacctgccca ttcgaccacc aagcgaaaca     780
tcgcatcgag cgagcacgta ctcggatgga agccggtctt gtcgatcagg atgatctgga     840
cgaagagcat caggggctcg cgccagccga actgttcgcc aggctcaagg cgcggatgcc     900
cgacggcgag gatctcgtcg tgacccatgg cgatgcctgc ttgccgaata tcatggtgga     960
aaatggccgc ttttctggat tcatcgactg tggccggctg ggtgtggcgg accgctatca    1020
ggacatagcg ttggctaccc gtgatattgc tgaagagctt ggcggcgaat gggctgaccg    1080
cttcctcgtg ctttacggta tcgccgctcc cgattcgcag cgcatcgcct tctatcgcct    1140
tcttgacgag ttcttctgag cgggactctg gggttcgcta gagggatcgat cctttttaac    1200
ccatcacata tacctgccgt tcactattat ttagtgaaat gagatattat gatattttct    1260
gaattgtgat taaaaaggca actttatgcc catgcaacag aaactataaa aaatacagag    1320
aatgaaaaga aacagataga ttttttagtt ctttaggccc gtagtctgca aatcctttta    1380
tgattttcta tcaaacaaaa gaggaaaata gaccagttgc aatccaaacg agagtctaat    1440
agaatgaggt cgaaaagtaa atcgcgcggg tttgttactg ataaagcagg caagacctaa    1500
aatgtgtaaa gggcaaagtg tatactttgg cgtcacccct tacatatttt aggtctttt     1560
ttattgtgcg taactaactt gccatcttca acaggaggg ctggaagaag cagaccgcta    1620
acacagtaca taaaaagga gacatgaacg atgaacatca aaagtttgc aaaacaagca     1680
acagtattaa cctttactac cgcactgctg gcaggaggcg caactcaagc gtttgcgaaa    1740
gaaacgaacc aaaagccata taggaaaaca tacggcattt cccatattac acgccatgat    1800
atgctgcaaa tccctgaaca gcaaaaaaat gaaaaatatc aagtttctga atttgattcg    1860
tccacaatta aaaatatctc ttctgcaaaa ggcctggacg tttgggacag ctggccatta    1920
caaaacgctg acggcactgt cgcaaactat cacggctacc acatcgtctt tgcattagcc    1980
ggagatccta aaaatgcgga tgacacatcg atttacatgt tctatcaaaa agtcggcgaa    2040
acttctattg acagctggaa aaacgctggc gcgtctttta agacagcga caaattcgat    2100
gcaaatgatt ctatcctaaa agaccaaaca caagaatggt caggttcagc cacatttaca    2160
tctgacggaa aaatccgttt attctacact gatttctccg gtaaacatta cggcaaacaa    2220
```

```
acactgacaa ctgcacaagt taacgtatca gcatcagaca gctctttgaa catcaacggt    2280
gtagaggatt ataaatcaat ctttgacggt gacggaaaaa cgtatcaaaa tgtacagcag    2340
ttcatcgatg aaggcaacta cagctcaggc gacaaccata cgctgagaga tcctcactac    2400
gtagaagata aaggccacaa atacttagta tttgaagcaa acactggaac tgaagatggc    2460
taccaaggcg aagaatcttt atttaacaaa gcatactatg gcaaaagcac atcattcttc    2520
cgtcaagaaa gtcaaaaact tctgcaaagc gataaaaaac gcacggctga gttagcaaac    2580
ggcgctctcg gtatgattga gctaaacgat gattacacac tgaaaaaagt gatgaaaccg    2640
ctgattgcat ctaacacagt aacagatgaa attgaacgcg cgaacgtctt taaaatgaac    2700
ggcaaatggt acctgttcac tgactcccgc ggatcaaaaa tgacgattga cggcattacg    2760
tctaacgata tttacatgct tggttatgtt tctaattctt taactggccc atacaagccg    2820
ctgaacaaaa ctggccttgt gttaaaaatg gatcttgatc taacgatgt aaccttact     2880 tactcacact tcgctgtacc tcaagcgaaa ggaaacaatg tcgtgattac aagctatatg    2940
acaaacagag gattctacgc agacaaacaa tcaacgtttg cgccgagctt cctgctgaac    3000
atcaaaggca agaaaacatc tgttgtcaaa gacagcatcc ttgaacaagg acaattaaca    3060
gttaacaaat aaaaacgcaa aagaaaatgc cgatgggtac cgagcgaaat gaccgaccaa    3120
gcgacgccca acctgccatc acgagatttc gattccaccg ccgccttcta tgaaaggttg    3180
ggcttcggaa tcgttttccg ggacgccctc gcggacgtgc tcatagtcca cgacgcccgt    3240
gattttgtag ccctggccga cggccagcag gtaggccgac aggctcatgc cggccgccgc    3300
cgccttttcc tcaatcgctc ttcgttcgtc tggaaggcag tacaccttga taggtgggct    3360
gcccttcctg gttggcttgg tttcatcagc catccgcttg ccctcatctg ttacgccggc    3420
ggtagccggc cagcctcgca gagcaggatt cccgttgagc accgccaggt gcgaataagg    3480
gacagtgaag aaggaacacc cgctcgcggg tgggcctact tcacctatcc tgccccgctg    3540
acgccgttgg ataccaag gaaagtctac acgaaccctt tggcaaaatc ctgtatatcg    3600
tgcgaaaaag gatggatata ccgaaaaaat cgctataatg accccgaagc agggttatgc    3660 agcgaaaag cgctgcttcc ctgctgtttt gtggaatatc taccgactgg aaacaggcaa    3720
atgcaggaaa ttactgaact gaggggacag gcgagagacg atgccaaaga gctcctgaaa    3780
atctcgataa ctcaaaaaat acgcccggta gtgatcttat tcattatgg tgaaagttgg    3840 aacctcttac gtgccgatca acgtctcatt ttcgccaaaa gttggcccag ggcttcccgg    3900
tatcaacagg gacaccagga tttatttatt ctgcgaagtg atcttccgtc acaggtattt    3960
attcggcgca aagtgcgtcg ggtgatgctg ccaacttact gatttagtgt atgatggtgt    4020
ttttgaggtg ctccagtggc ttctgtttct atcagctcct gaaaatctcg ataactcaaa    4080
aaatacgccc ggtagtgatc ttatttcatt atggtgaaag ttggaacctc ttacgtgccg    4140
atcaacgtct cattttcgcc aaaagttggc ccagggcttc ccggtatcaa cagggacacc    4200
aggatttatt tattctgcga agtgatcttc cgtcacaggt atttattcgg cgcaaagtgc    4260
gtcgggtgat gctgccaact tactgattta gtgtatgatg gtgtttttga ggtgctccag    4320
tggcttctgt ttctatcagg gctggatgat cctccagcgc ggggatctca tgctggagtt    4380
cttcgcccac cccaaaagga tctaggtgaa gatccttttt gataatctca tgaccaaaat    4440
cccttaacgt gagttttcgt tccactgagc gtcagacccc gtagaaaaga tcaaaggatc    4500
ttcttgagat cctttttttc tgcgcgtaat ctgctgcttg caaacaaaaa aaccaccgct    4560
accagcggtg gtttgtttgc cggatcaaga gctaccaact cttttttccga aggtaactgg    4620
```

-continued

```
cttcagcaga gcgcagatac caaatactgt ccttctagtg tagccgtagt taggccacca    4680
cttcaagaac tctgtagcac cgcctacata cctcgctctg ctaatcctgt taccagtggc    4740
tgctgccagt ggcgataagt cgtgtcttac cgggttggac tcaagacgat agttaccgga    4800
taaggcgcag cggtcgggct gaacgggggg ttcgtgcaca cagcccagct tggagcgaac    4860
gacctacacc gaactgagat acctacagcg tgagcattga gaaagcgcca cgcttcccga    4920
agggagaaag gcgacaggt atccggtaag cggcagggtc ggaacaggag agcgcacgag     4980
ggagcttcca gggggaaacg cctggtatct ttatagtcct gtcgggtttc gccacctctg    5040
acttgagcgt cgatttttgt gatgctcgtc aggggggcgg agcctatgga aaaacgccag    5100
caacgcggcc tttttacggt tcctggcctt ttgctggcct tttgctcaca tgttctttcc    5160
tgcgttatcc cctgattctg tggataaccg tattaccgcc tttgagtgag ctgataccgc    5220
tcgccgcagc cgaacgaccg agcgcagcga gtcagtgagc gaggaagcgg aagagcgccc    5280
aatacgcaaa ccgcctctcc ccgcgcgttg gccgattcat taatgcagct ggcacgacag    5340
gtttcccgac tggaaagcgg gcagtgagcg caacgcaatt aatgtgagtt agctcactca    5400
ttaggcaccc caggctttac actttatgct tccggctcgt atgttgtgtg gaattgtgag    5460
cggataacaa tttcacacag gaaacagcta tgaccatgat tacgaattcg agctcggtac    5520
ccggggatcc cgactttggc ctgggtaggt tatatccccc agaggtgctt ctaatgggtt    5580
ttgagggcct tgggcatacg aaaaatcatt tgagaaaact cgaggcatga aacaggctct    5640
atattcctat cacccacgaa accggtggca agaattttca acatcgtgga attcttgcca    5700
ccggtttgta gagcctaggg ggaggcgtcg taaagcttaa acgccgccag ccaggactgc    5760
ctcgtggttg acgtccagcg cgcggtttac ggcggaggtc actgccttca gcgaagcgta    5820
ggtgatggag ccagcgatgc cgacgcccca gaccttgcgg ccgttgacct cagccagcac    5880
gtaggcggct gcttctgcat cgtcgcccga ggtgcgggcg tgctggttgt cttcctggat    5940
ctcaacgtcg atgcccagct tctccagcgc gttggcgtaa gcggccagtg ggccgttgcc    6000
gcggccatcg acggtgacgt ccttgccgtt gtggatgagc tcggcggtga tggatgcatc    6060
ctcgttttcg gtctgagcgt tctcgacgcg cagcgcgatc tgctcaactg gtgcggtgcg    6120
ctccaggtac tcggtggcga agatatccca cattgccttg gagttgacct cgccgccctc    6180
agcgtcggtg acgttctgga caacggtgga gaactcaacc tgcatggagc gagggatctg    6240
cagaccgtga tcggtcttca tgatgtaagc aacgccgccc ttgccggact gggagttcac    6300
gcggataaca gcctcgtagt cgcgaccgac gcatgcaagc ttggcactgg ccgtcgtttt    6360
acaacgtcgt gactgggaaa accctggcgt tacccaactt aatcgccttg cagcacatcc    6420
ccctttcgcc agctggcgta atagcgaaga ggcccgcacc gatcgccctt cccaacagtt    6480
gcgcagcctg aatggcgaat ggcg                                           6504
```

FEEDBACK-RESISTANT ALPHA-ISOPROPYLMALATE SYNTHASES

CROSS REFERENCE TO RELATED APPLICATIONS

This application is a National Phase filing under 35 U.S.C. §371 of PCT/EP2013/057660 filed on Apr. 12, 2013; and this application claims priority to Application No. 10 2012 207 097.4 filed in Germany on Apr. 27, 2012, under 35 U.S.C. §119; the entire contents of each application is hereby incorporated by reference.

The invention relates to an isolated nucleotide sequence encoding an amino acid sequence that is at least ≥90%, ≥92%, ≥94%, ≥96%, ≥97%, ≥98%, ≥99% or 100%, preferably ≥97%, particularly preferably ≥98%, very particularly preferably ≥99%, and extremely preferably 100%, identical to the amino acid sequence of SEQ ID NO:2, wherein SEQ ID NO:2, at position 553, or at a corresponding position of the amino acid sequence, has a proteinogenic amino acid other than L-tyrosine, to a microorganism comprising the nucleotide sequence and also to a process for producing fine chemicals using this microorganism.

Fine chemicals, which include, in particular, amino acids, organic acids, vitamins, nucleosides and nucleotides, are used in human medicine, in the pharmaceuticals industry, in cosmetics, in the food industry and in animal feeding.

A great number of these compounds are produced by fermentation of strains of coryneform bacteria, in particular *Corynebacterium glutamicum*. Because of the great importance thereof, work is constantly underway on improving the production process. Process improvements can relate to fermentation measures, such as, for example, agitation and supply with oxygen, or the composition of the nutrient media such as, for example, the sugar concentration during fermentation, or workup to give the product form by, for example, ion-exchange chromatography, or the intrinsic performance properties of the microorganism itself.

Methods of mutagenesis, screening and mutant selection are employed for improving the performance properties of said microorganisms. In this manner strains are obtained that are resistant to antimetabolites such as, e.g., the leucine analogue 4-azaleucine or 5,5,5-trifluoroleucine and produce chemical compounds, for example L-amino acids such as L-leucine. By way of example, mention may be made of the literature reference Casalone et al. (Research in Microbiology 148: 613-623 1997).

For some years, likewise, methods of recombinant DNA technology have been used for strain improvement of L-amino acid-producing strains of *Corynebacterium glutamicum*, in that, for example, individual amino acid biosynthesis genes are amplified or attenuated and the effect on the production of the chemical compound is studied.

Summarizing presentations on the biology, genetics and biotechnology of *Corynebacterium glutamicum* may be found in the "Handbook of *Corynebacterium glutamicum*" (Eds.: L. Eggeling and M. Bott, CRC Press, Taylor & Francis, 2005), in the special issue of the Journal of Biotechnology (Chief Editor: A. Pühler) with the title "A New Era in *Corynebacterium glutamicum* Biotechnology" (Journal of Biotechnology 104/1-3, (2003)) and in the book by T. Scheper (Managing Editor) "Microbial Production of L-Amino Acids" (Advances in Biochemical Engineering/Biotechnology 79, Springer Verlag, Berlin, Germany, 2003).

The nucleotide sequence of the genome of *Corynebacterium glutamicum* is described in Ikeda and Nakagawa (Applied Microbiology and Biotechnology 62, 99-109 (2003)), in EP 1 108 790 and in Kalinowski et al. (Journal of Biotechnology 104/1-3, (2003)).

The nucleotide sequences of the genome of *Corynebacterium glutamicum* are likewise available in the database of the National Center for Biotechnology Information (NCBI) of the National Library of Medicine (Bethesda, Md., USA), in the DNA Data Bank of Japan (DDBJ, Mishima, Japan) or in the nucleotide sequence database of the European Molecular Biologies Laboratories (EMBL, Heidelberg, Germany or Cambridge, UK).

The leuA gene encoding the α-isopropylmalate synthase from *Corynebacterium glutamicum* is described, inter alia, by the following details:

The α-isopropylmalate synthase (IPMS, EC=2.3.3.13) catalyses the condensation of the acetyl group of acetyl-CoA with 3-methyl-2-oxobutanoate (2-oxoisovalerate, ketoisovalerate) for the formation of 3-carboxy-3-hydroxy-4-methylpentanoate (2-isopropylmalate). The leuA gene comprises 1851 base pairs (bp) and encodes a polypeptide having an M(r) of 68 187. As is widespread for enzymes that catalyse the first step of a biosynthesis pathway, the α-isopropylmalate synthase is subject to feedback regulation by the end product leucine (Patěk et al., Applied Environmental Microbiology 60:133-140 (1994)). Furthermore, the enzyme is inhibited by coenzyme A in the presence of divalent cations, especially zinc (Ulm et al., Journal of Bacteriology 110(3): 1118-1126 (1972); Tracy and Kohlhaw, Proceedings of the National Academy of Sciences of the United States of America 72(5): 1802-1806 (1975)).

The nucleotide sequence of the leuA gene encoding the α-isopropylmalate synthase from *Corynebacterium glutamicum*, according to the details of the NCBI Database, is represented in SEQ ID NO:1 and the amino acid sequence resulting therefrom of the encoded α-isopropylmalate synthase in SEQ ID NO: 4. In SEQ ID NO:3, nucleotide sequences situated upstream and downstream are reported additionally.

The object of the invention is to provide a fermentative process for producing ketoisocaproate or L-leucine having an improved yield or a higher end concentration of the product intracellularly and/or in the medium.

A further object of the invention is to provide a cell which is modified in such a manner that, even in the presence of high intracellular concentrations of leucine, is capable of producing ketoisocaproate or leucine.

A further object of the invention is to improve the yield of ketoisocaproate or leucine, based on the amount of the carbon substrate used for the fermentation.

The inventors of the present invention have surprisingly established that a mutation of the α-isopropylmalate synthase leads to an increase in the production of ketoisocaproate and leucine. Without wishing to be bound to any theory, the inventors suspect that this mutation decreases or even eliminates the feedback inhibition of the enzyme, i.e. the reduction in enzyme activity mediated by binding the product to the enzyme.

The expression "leucine", which is used synonymously with "L-leucine", also includes the salts thereof such as, for example, L-leucine hydrochloride, L-leucine sulphate or the calcium salt. Likewise, the expression ketoisocaproate (KIC) also comprises salts thereof such as, for example, calcium-KIC, potassium-KIC or sodium-KIC.

The invention relates to an isolated nucleotide sequence encoding an amino acid sequence that is at least ≥90%, ≥92%, ≥94%, ≥96%, ≥97%, ≥98%, ≥99% or 100%, preferably ≥97%, particularly preferably ≥98%, very particularly preferably ≥99%, and extremely preferably 100%, identical to the amino acid sequence of SEQ ID NO:2, wherein SEQ ID NO:2, at position 553, or at a corresponding position of the amino acid sequence, has a proteinogenic amino acid other than L-tyrosine.

In a preferred embodiment, the amino acid sequence encoded by the nucleic acid sequence according to the invention has, at the position 553 or a corresponding position, an amino acid which is selected from the group consisting of glutamic acid, aspartic acid, alanine, cysteine, serine, threonine, lysine, arginine, glutamine and asparagine, particularly preferably from the group consisting of glutamic acid and aspartic acid.

In a preferred embodiment, the amino acid sequence encoded by the nucleic acid sequence according to the invention has, at position 553 or a corresponding position, L-aspartic acid.

In a preferred embodiment, the nucleic acid sequence according to the invention is a nucleic acid sequence having guanine at position 1657 or a corresponding position, represented in SEQ ID NO:5.

The expression "a position corresponding to position 553 of the amino acid sequence" or "a position comparable with position 553 of the amino acid sequence" is taken to mean the fact that, by insertion or deletion of a codon encoding an amino acid in the N-terminal region (based on position 553 of SEQ ID NO:2) of the encoded polypeptide, the positional statement and length statement in the case of an insertion is formally increased by one unit, or, in the case of a deletion, decreased by one unit. In the same manner, by insertion or deletion of a codon encoding an amino acid in the C-terminal region (based on position 553) of the encoded polypeptide, the length statement, in the case of an insertion, is formally increased by one unit, or, in the case of a deletion, decreased by one unit. Such comparable positions may be readily identified by comparison of the amino acid sequences in the form of an "alignment", for example using the Clustal W Programme (Thompson et al., Nucleic Acids Research 22, 4637-4680 (1994)) or the MAFFT Programme (Katoh et al., Genome Information 2005; 16(1), 22-33).

Such insertions and deletions do not affect the enzymatic activity substantially. "Do not affect substantially" means that the enzymatic activity of said variants differs by a maximum of 10%, a maximum of 7.5%, a maximum of 5%, a maximum of 2.5%, or a maximum of 1%, from the activity of the polypeptide having the amino acid sequence of SEQ ID NO:2.

A method for determining the enzymatic activity of isopropylmalate synthase is described in Kohlhaw et al. (Methods in Enzymology 166:423-9 (1988)); the test is based on measuring the change in extinction at 412 nm due to thionitrobenzoate (TNB) formed from DTNB (5,5'-dithiobis-(2-nitrobenzoic acid), Ellman's reagent) by reduction with CoA.

The invention correspondingly also relates to nucleotide sequences and nucleic acid molecules comprising such sequences and encoding polypeptide variants of SEQ ID NO:2 or 6, which contain one or more insertion(s) or deletion(s). Preferably, the polypeptide contains a maximum of 5, a maximum of 4, a maximum of 3, or a maximum of 2, insertions or deletions of amino acids.

Preference is given to replicable nucleotide sequences encoding the enzyme isopropylmalate synthase that are isolated from microorganisms of the genus *Corynebacterium*, in particular *Corynebacterium glutamicum*, wherein the protein sequences encoded thereby contain a proteinogenic amino acid other than L-tyrosine at the position corresponding to position 553 of SEQ ID NO:2.

Particular preference, furthermore, is given to a replicable nucleotide sequence (DNA) encoding the enzyme isopropylmalate synthase and which is isolated from microorganisms of the genus *Corynebacterium*, in particular *Corynebacterium glutamicum*, wherein the associated amino acid sequence contains, at position 553, L-aspartic acid, represented in SEQ ID NO:6.

The invention further relates to a replicable nucleotide sequence (DNA) encoding the enzyme isopropylmalate synthase and which is isolated from microorganisms of the genus *Corynebacterium*, in particular *Corynebacterium glutamicum*, the base sequence of which nucleotide sequence contains, at position 1657, guanine, illustrated in SEQ ID NO:5.

The invention further relates to plasmids and vectors that comprise the nucleotide sequences according to the invention and optionally replicate in microorganisms of the genus *Corynebacterium* or are suitable therefor.

The invention further relates to microorganisms of the genus *Corynebacterium* that comprise the nucleotide sequences, vectors and polypeptides according to the invention.

The invention further relates to a polypeptide comprising an amino acid sequence encoded by the nucleotide sequence according to the invention. An exemplary polypeptide is represented in SEQ ID NO 6.

In a particularly preferred embodiment, the polypeptide according to the invention or the polypeptide encoded by the nucleotide sequence according to the invention or the polypeptide which the microorganism comprises according to the invention is a modified IPMS having reduced feedback inhibition relative to the wild-type enzyme, i.e. the enzyme is less inhibited than the wild-type enzyme by one of its products or a metabolite formed therefrom in metabolism, for example KIC or L-leucine.

The invention preferably further relates to microorganisms of the genus *Corynebacterium* that comprise the nucleotide sequences, vectors and/or polypeptides according to the invention and in which microorganisms the nucleotide sequences encoding the isopropylmalate synthase are present preferably in overexpressed form.

The invention further relates particularly preferably to microorganisms of the genus *Corynebacterium* that contain the nucleotide sequences according to the invention and in which the nucleotide sequences encoding the isopropylmalate synthase are present preferably in overexpressed form, wherein the associated amino acid sequence contains L-aspartic acid at position 553, represented in SEQ ID NO:6.

For generating the nucleotide sequences according to the invention that encode α-isopropylmalate synthase characterized by an amino acid exchange at position 553 of SEQ ID NO:2, mutagenesis methods described in the prior art are used.

For the mutagenesis, in-vitro methods such as, for example, mutagenic oligonucleotides (T. A. Brown: Gentechnologie für Einsteiger [Genetic engineering for beginners], Spektrum Akademischer Verlag, Heidelberg, 1993) or the polymerase chain reaction (PCR), as described in the handbook by Newton and Graham (PCR, Spektrum Akademischer Verlag, Heidelberg, 1994), can be used.

Further instructions for generating mutations can be found in the prior art and known textbooks of genetics and molecular biology such as, e.g., the textbook by Knippers ("Molekulare Genetik" [Molecular genetics], 6$^{th}$ edition, Georg Thieme Verlag, Stuttgart, Germany, 1995), that by Winnacker ("Gene and Klone" [Genes and clones], VCH Verlagsgesellschaft, Weinheim, Germany, 1990) or that by Hagemann ("Allgemeine Genetik" [General genetics], Gustav Fischer Verlag, Stuttgart, 1986).

When in-vitro methods are used, the leuA gene described in the prior art, starting from isolated total DNA of a wild-type strain, is amplified using the polymerase chain reaction, optionally cloned into suitable plasmid vectors, and the DNA is then subjected to the mutagenesis process. Instructions for amplifying DNA sequences using the polymerase chain reaction (PCR) may be found by those skilled in the art, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). Suitable leuA alleles are then isolated, studied and sequenced. Instructions for this purpose may be found, for example, in Kalinowski et al. (Molecular and General Genetics 224: 317-324 (1990)), Kalinowski et al. (Molecular Microbiology 5:1197-204 (1991)) or Follettie et al. (Journal of Bacteriology 175, 4096-4103 (1993)). Instructions on sequencing may be found, for example, in Sanger et al. (Proceedings of the National Academy of Sciences of the United States of America, 74:5463-5467, (1977)).

The invention therefore relates to an isolated polynucleotide encoding the enzyme isopropylmalate synthase, which isolated polynucleotide comprises a polynucleotide having the nucleotide sequence represented in SEQ ID NO:5.

The invention further relates to an isolated polynucleotide encoding the enzyme isopropylmalate synthase, which isolated polynucleotide comprises the nucleotide sequence represented in SEQ ID NO:5 or consists thereof.

Details on the biochemistry or chemical structure of nucleotide sequences as occur in living creatures, such as, for example, microorganisms, may be found, inter alia, in the textbook "Biochemie" [Biochemistry] by Berg et al. (Spektrum Akademischer Verlag Heidelberg, Berlin, Germany, 2003; ISBN 3-8274-1303-6).

In a preferred embodiment, the expression "nucleotide sequence" or "amino acid sequence" is taken to mean nucleic acid molecules from the group comprising DNA, RNA and modified forms thereof, or polypeptides that comprise the specified sequence, for example in fusion with another sequence, or consist thereof.

If the nucleotide sequence consists of deoxyribonucleotide monomers having the nucleobases or bases adenine (A), guanine (G), cytosine (C) and thymine (T), then this is described as deoxyribonucleotide sequence or deoxyribonucleic acid (DNA). If the nucleotide sequence consists of ribonucleotide monomers having the nucleobases or bases adenine (A), guanine (G), cytosine (C) and uracil (U), then this is described as ribonucleotide sequence or ribonucleic acid (RNA). In said nucleotide sequences, the monomers are covalently bound to one another via a 3'→5'-phosphodiester bond.

A gene, from the chemical viewpoint, is a nucleotide sequence. A nucleotide sequence that encodes a protein/polypeptide is here used synonymously with the expression "gene". The two expressions "gene" and "encoding region" are used synonymously and, in the same way, the two expressions "protein" and "polypeptide".

"Proteinogenic amino acids" are taken to mean the amino acids that occur in natural proteins, that is to say in proteins from microorganisms, plants, animals and humans. They serve as structural units for proteins in which they are linked to one another via peptide bonds.

If, hereinafter, proteinogenic L-amino acids are mentioned, this means one or more of the amino acids including salts thereof selected from the group L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and, optionally, L-selenocysteine and L-pyrrolysine. The L-amino acids likewise include L-homoserine. Particular preference is given to the L-amino acid L-leucine.

Overexpression is taken to mean, generally, an increase in the intracellular concentration or activity of a ribonucleic acid, a protein (polypeptide) or an enzyme, compared with the starting strain (parent strain) or wild-type strain, if this is the starting strain. A starting strain (parent strain) is taken to mean the strain on which the measure leading to the overexpression was carried out.

In the overexpression, the methods of recombinant overexpression are preferred. These include all methods in which a microorganism is produced using a DNA molecule provided in vitro. Such DNA molecules comprise, for example, promoters, expression cassettes, genes, alleles, encoding regions etc. These are converted into the desired microorganism by methods of transformation, conjugation, transduction or like methods.

The extent of the expression or overexpression can be established by measuring the amount of the mRNA transcribed by the gene, by determining the amount of the polypeptide, and by determining the enzyme activity.

For determining the amount of mRNA, inter alia, the method of Northern Blotting and quantitative RT-PCR can be used. In quantitative RT-PCR, a reverse transcription is connected upstream of the polymerase chain reaction. For this purpose, the LightCycler™ System from Roche Diagnostics (Boehringer Mannheim GmbH, Roche Molecular Biochemicals, Mannheim, Germany) can be used, as described, for example, in Jungwirth et al. (FEMS Microbiology Letters 281, 190-197 (2008)). The concentration of the protein can be determined by 1- and 2-dimensional protein gel separation and subsequent optical identification of the protein concentration in the gel using corresponding evaluation software. A common method for preparation of the protein gels for coryneform bacteria and for identifying the proteins is the procedure described by Hermann et al. (Electrophoresis, 22:1712-23 (2001)). The protein concentration can likewise be determined by Western-blot hybridization with an antibody specific for the protein that is to be detected (Sambrook et al., Molecular cloning: a laboratory manual. $2^{nd}$ Ed. Cold Spring Harbor Laboratory Press, Cold Spring Harbor, N.Y., 1989) and subsequent optical evaluation with corresponding software for determining the concentration (Lohaus and Meyer (1998) Biospektrum 5:32-39; Lottspeich, Angewandte Chemie 321: 2630-2647 (1999)). The statistical significance of the data obtained is determined using a T test (Gosset, Biometrika 6(1): 1-25 (1908)).

For achieving overexpression, in the prior art, a multiplicity of methods are available. These include, in addition to modifying the nucleotide sequences that control the expression of the gene, also increasing the copy number.

The copy number can be increased by plasmids which replicate in the cytoplasm of the microorganism. For this purpose, in the prior art, an abundance of plasmids are described for the most varied groups of microorganisms, with which plasmids the desired increase in copy number of the gene can be set. Suitable plasmids for the genus *Corynebacterium* are described, for example, in Tauch et al. (Journal of Biotechnology 104 (1-3), 27-40, (2003)), or in Stansen et al. (Applied and Environmental Microbiology 71, 5920-5928 (2005)).

The copy number can additionally be increased by at least one (1) copy by inserting further copies into the chromosome of the microorganism. Suitable methods for the genus *Corynebacterium* are described, for example, in the patent documents WO 03/014330, WO 03/040373 and WO 04/069996.

Gene expression can additionally be increased in that a plurality of promoters are positioned upstream of the desired gene, or are functionally linked to the gene that is to be expressed and in this manner increased expression is achieved. Examples thereof are described in the patent document WO 2006/069711.

Transcription of a gene may be controlled by proteins that suppress transcription (repressor proteins) or promote it (activator proteins). Therefore, to achieve overexpression, it is likewise possible to increase the expression of activator proteins or to reduce the expression of repressor proteins or to turn them off or else to eliminate the binding sites of the repressor proteins.

The rate of elongation is affected by codon usage; the use of codons for transfer (t)-RNAs frequently occurring in the starting strain can amplify the translation. In addition, the exchange of a start codon for the codon ATG most frequently occurring in many microorganisms (77% in *Escherichia coli*) can considerably enhance translation, since, at the RNA level, the codon AUG is two to three times more effective than, for example, the codons GUG and UUG (Khudyakov et al., FEBS Letters 232(2):369-71 (1988); Reddy et al., Proceedings of the National Academy of Sciences of the USA 82(17): 5656-60 (1985)). Also, the sequence environment of the start codon can be optimized since interactive effects between the start codon and the flanking regions have been described (Stenstrom et al., Gene 273(2):259-65 (2001); Hui et al., EMBO Journal 3(3):623-9 (1984)).

Instructions on handling DNA, digestion and ligation of DNA, transformation and screening of transformants may be found, inter alia, in the known handbook by Sambrook et al. "Molecular Cloning: A Laboratory Manual", Second Edition (Cold Spring Harbor Laboratory Press, 1989).

The invention also relates to vectors that comprise the polynucleotide according to the invention.

Kirchner and Tauch (Journal of Biotechnology 104:287-299 (2003)) describe a selection of the vectors to be employed in *Corynebacterium glutamicum*.

The invention further relates to a microorganism according to the invention, characterized in that the nucleotide sequence according to the invention is integrated in a chromosome. Homologous recombination permits, with use of the vectors according to the invention, the exchange of DNA sections on the chromosome for polynucleotides according to the invention which are transported into the cell by the vector. For efficient recombination between the ring-type DNA molecule of the vector and the target DNA on the chromosome, the DNA region that is to be exchanged containing the polynucleotide according to the invention is provided at the ends with nucleotide sequences homologous to the target site; these determine the site of integration of the vector and of exchange of the DNA.

For instance, the polynucleotide according to the invention can be exchanged for the native leuA gene at the native gene site in the chromosome, or integrated at a further gene site.

Expression or overexpression is preferably carried out in microorganisms of the genus *Corynebacterium*. Within the genus *Corynebacterium*, strains are preferred which are based on the following species: *Corynebacterium efficiens*, wherein the type strain is deposited as DSM44549, *Corynebacterium glutamicum*, wherein the type strain is deposited as ATCC13032, and *Corynebacterium ammoniagenes*, wherein the type strain is deposited as ATCC6871. The species *Corynebacterium glutamicum* is very particularly preferred.

Some members of the species *Corynebacterium glutamicum* are also known in the prior art under other names. These include, for example: strain ATCC13870, which has been termed *Corynebacterium acetoacidophilum*, strain DSM20137, which has been termed *Corynebacterium lilium*, strain ATCC17965, which has been termed *Corynebacterium melassecola*, strain ATCC14067, which has been termed *Brevibacterium flavum*, strain ATCC13869, which has been termed *Brevibacterium lactofermentum*, and strain ATCC14020, which has been termed *Brevibacterium divaricatum*.

The expression "*Micrococcus glutamicus*" for *Corynebacterium glutamicum* has likewise been used. Some members of the species *Corynebacterium efficiens* have also been called in the prior art *Corynebacterium thermoaminogenes*, such as, for example, strain FERM BP-1539.

The microorganisms or strains (starting strains) used for the measures of introducing a feedback-resistant IPMS preferably already possess the capability of secreting KIC or L-leucine into the surrounding nutrient medium and accumulating it there. For this process, hereinafter, the expression "producing" is also used. In particular, the strains used for the overexpression measures possess the capability of accumulating in the cell or in the nutrient medium (≥ means at least) ≥0.10 g/l, 0.25 g/l, ≥0.5 g/l, ≥1.0 g/l, ≥1.5 g/l, ≥2.0 g/l, ≥4 g/l or ≥10 g/l of L-leucine or KIC in (≤ means at most)≤120 hours, ≤96 hours, −48 hours, ≤36 hours, ≤24 hours or ≤12 hours. The starting strains are preferably strains which were produced by mutagenesis and screening, by recombinant DNA techniques or by a combination of both methods.

It is understandable to those skilled in the art that it is also possible to arrive at a microorganism suitable for the measures of the invention in that, in a wild strain, such as, for example, in the *Corynebacterium glutamicum* type strain ATCC 13032 or in the strain ATCC 14067, first the polynucleotide according to the invention according to SEQ ID NO:5 is inserted and then the microorganism is caused, by further genetic measures described in the prior art, to produce the desired KIC or L-leucine.

Information on the taxonomic classification of strains of this group of bacteria may be found, inter alia, in Seiler (Journal of General Microbiology 129, 1433-1477 (1983)), Kinoshita (1985, Glutamic Acid Bacteria, p. 115-142. In: Demain and Solomon (ed), Biology of Industrial Microorganisms. The Benjamin/Cummins Publishing Co., London, UK), Kämpfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains having the designation "ATCC" can be obtained from the American Type Culture Collection (Manassas, Va., USA). Strains having the designation "DSM" can be obtained from the German Collection of Microorganisms and Cell Cultures (DSMZ, Brunswick, Germany). Strains having the designation "NRRL" can be obtained from the Agricultural Research Service Patent Culture Collection (ARS, Peoria, Ill., US). Strains having the designation "FERM" can be obtained from the National Institute of Advanced Industrial Science and Technology (AIST Tsukuba Central 6, 1-1-1 Higashi, Tsukuba Ibaraki, Japan).

KIC-secreting or -producing strains are based, for example, on:
*Corynebacterium glutamicum*, strain ATCC13032,
*Brevibacterium flavum*, strain ATCC 14067 and
*Brevibacterium lactofermentum*, strain ATCC 13869.

In combination with the production of ketoisocaproate, in addition, preferably one or more genes of the nucleotide sequences are (over)expressed that encode enzymes of the biosynthesis of ketoisocaproate, selected from the group:
a) polynucleotides (ilvB gene and ilvN gene) that encode the subunits of an acetolactate synthase (IlvBN, EC No.: 4.1.3.18)
b) polynucleotide (ilvC gene) that encodes an isomeroreductase (IlvC, EC No.: 1.1.1.86)
c) polynucleotide (ilvD gene) that encodes a dihydroxy acid dehydratase (IlvD, EC No.: 4.2.1.9)
d) polynucleotide (ilvE gene) that encodes a transaminase (IlvE, EC No.: 2.6.1.42)
e) polynucleotide (leuA gene) that encodes an isopropylmalate synthase (leuA, EC No.: 2.3.3.13)
f) polynucleotide (leuB gene) that encodes an isopropylmalate dehydrogenase (leuB, EC No.: 1.1.1.85)
g) polynucleotide (leuC gene) that encodes the large subunit of an isopropylmalate isomerase (leuC, EC No.: 4.2.1.33)
h) polynucleotide (leuD gene) that encodes the small subunit of an isopropylmalate isomerase (leuD, EC No.: 4.2.1.33)
wherein the genes ilvBN, ilvC, ilvD, leuA, leuB, leuC and leuD are particularly preferred for α-ketoisocaproic acid (KIC).

The present invention provides a microorganism which produces KIC or L-leucine, wherein the microorganism has a feedback-resistant α-isopropylmalate synthase owing to the use of the polynucleotide according to the invention according to SEQ ID NO: 5.

Fermentative process for producing the fine chemical KIC or L-leucine comprising the following steps:
a) fermentation of one of the microorganisms according to any one of Claim 7 to 12 in a medium,
b) accumulation of the KIC or L-leucine in the medium, wherein a fermentation broth is obtained. In this case it is preferred that the fine chemical or a liquid or solid fine chemical-containing product is obtained from the fine chemical-containing fermentation broth.

The use of such a process according to the invention leads, as shown in Example 4 with reference to ketoisocaproate production or as shown in Example 5 with reference to L-leucine production, to an extraordinary increase in yield compared with the respective starting strain (Example 4, KIC: 0.027 g/g vs. 0.012 g/g; Example 5, leucine: 0.041 g/g vs. 0.002 g/g).

In addition, it is particularly preferred that the microorganism according to the invention produces KIC or L-leucine, still more preferably secretes KIC or L-leucine into the medium. The microorganisms produced can be cultured continuously—as described, for example, in WO 05/021772—or discontinuously in the batch process (batch culturing or batch process) or in the fed-batch or repetitive fed-batch process for the purpose of production of the desired organic chemical compound. A summary of a general type on known culturing methods is available in the textbook by Chmiel (Bioprozesstechnik 1. Einführung in die Bioverfahrenstechnik [Process biotechnology 1. Introduction to bioengineering] (Gustav Fischer Verlag, Stuttgart, 1991)) or in the textbook by Storhas (Bioreaktoren and periphere Einrichtungen [Bioreactors and periphery equipment] (Vieweg Verlag, Brunswick/Wiesbaden, 1994)).

The culture medium or fermentation medium that is to be used must appropriately satisfy the demands of the respective strains. Descriptions of culture media of various microorganisms are contained in the handbook "Manual of Methods for General Bacteriology" of the American Society for Bacteriology (Washington D.C., USA, 1981). The terms culture medium and fermentation medium or medium are mutually exchangeable.

As carbon source, sugars and carbohydrates can be used, such as, e.g., glucose, sucrose, lactose, fructose, maltose, molasses, sucrose-containing solutions from beet sugar or sugar cane processing, starch, starch hydrolysate and cellulose, oils and fats, such as, for example, soybean oil, sunflower oil, groundnut oil and coconut fat, fatty acids, such as, for example, palmitic acid, stearic acid and linoleic acid, alcohols such as, for example, glycerol, methanol and ethanol, and organic acids, such as, for example, acetic acid or lactic acid.

As nitrogen source, organic nitrogen compounds such as peptones, yeast extract, meat extract, malt extract, corn-steep water, soybean meal and urea or inorganic compounds such as ammonium sulphate, ammonium chloride, ammonium phosphate, ammonium carbonate and ammonium nitrate can be used. The nitrogen sources can be used individually or as a mixture.

As phosphorus source, phosphoric acid, potassium dihydrogenphosphate or dipotassium hydrogenphosphate or the corresponding sodium-containing salts can be used.

The culture medium must, in addition, contain salts, for example in the form of chlorides or sulphates of metals such as, for example, sodium, potassium, magnesium, calcium and iron, such as, for example, magnesium sulphate or iron sulphate, which are necessary for growth. Finally, essential growth substances such as amino acids, for example homoserine and vitamins, for example thiamine, biotin or pantothenic acid, can be used in addition to the abovementioned substances.

Said starting materials can be added to the culture in the form of a single batch, or supplied in a suitable manner during the culturing.

Basic compounds such as sodium hydroxide, potassium hydroxide, ammonia or ammonia water, or acid compounds such as phosphoric acid or sulphuric acid, are used in a suitable manner for pH control of the culture. The pH is generally adjusted to 6.0 to 8.5, preferably 6.5 to 8. For control of foam development, antifoams can be used, such as, for example, polyglycol esters of fatty acids. For maintaining the stability of plasmids, suitable selectively acting substances such as, for example, antibiotics, can be added to the medium. The fermentation is preferably carried out under aerobic conditions. In order to maintain said aerobic conditions, oxygen or oxygen-containing gas mixtures such as, for example, air, are introduced into the culture. The use of liquids that are enriched with hydrogen peroxide is likewise possible. Optionally, the fermentation is carried out at superatmospheric pressure, for example at a superatmospheric pressure of 0.03 to 0.2 MPa. The temperature of the culture is usually 20° C. to 45° C., and preferably 25° C. to 40° C., particularly preferably 30° C. to 37° C. In the case of batch or fed-batch processes, the culturing is preferably continued until an amount sufficient for the measure of obtaining the desired organic chemical compound has formed. This goal is usually reached within 10 hours to 160 hours. In continuous processes, longer culture times are possible. Owing to the activity of the microorganisms, enrichment (accumulation) of the fine chemicals in the fermentation medium and/or in the cells of the microorganisms occurs.

Examples of suitable fermentation media may be found, inter alia, in patent documents U.S. Pat. No. 5,770,409, U.S. Pat. No. 5,990,350, U.S. Pat. No. 5,275,940, WO 2007/012078, U.S. Pat. No. 5,827,698, WO 2009/043803, U.S. Pat.

No. 5,756,345 or U.S. Pat. No. 7,138,266; appropriate modifications may optionally be carried out to the requirements of the strains used.

L-Amino acids can be analysed for determination of the concentration at one or more timepoints in the course of the fermentation by separation of the L-amino acids by way of ion-exchange chromatography, preferably cation-exchange chromatography, with subsequent post-column derivatization, using ninhydrin, as described in Spackman et al. (Analytical Chemistry 30: 1190-1206 (1958)). Instead of ninhydrin, ortho-phthaldialdehyde can also be used for post-column derivatization. A review article on ion-exchange chromatography may be found in Pickering (LC·GC (Magazine of Chromatographic Science) 7(6), 484-487 (1989)).

It is likewise possible to perform a pre-column derivatization, for example using ortho-phthaldialdehyde or phenylisothiocyanate, and to separate the resultant amino acid derivatives by reversed-phase chromatography (RP) preferably in the form of high-performance liquid chromatography (HPLC). Such a method is described, for example, in Lindroth et al. (Analytical Chemistry 51: 1167-1174 (1979)).

Detection proceeds photometrically (absorption, fluorescence).

A summarizing presentation on amino acid analysis may be found, inter alia, in the textbook "Bioanalytik" [Bioanalysis] by Lottspeich and Zorbas (Spektrum Akademischer Verlag, Heidelberg, Germany 1998).

Analysis of $\alpha$-keto acids such as KIC for determining the concentration at one or more timepoints in the course of the fermentation can be carried out by separating the keto acids and other secretion products by way of ion-exchange chromatography, preferably cation-exchange chromatography, on a sulphonated styrene-divinylbenzene polymer in the H+ form, e.g. using 0.025 N sulphuric acid with subsequent UV detection at 215 nm (alternatively, also at 230 or 275 nm). Preferably, a REZEX RFQ—Fast Fruit H+ column (Phenomenex) can be used; other suppliers for the separation phase (e.g. Aminex from BioRad) are possible. Similar separations are described in corresponding application examples of the suppliers.

The performance of the processes or fermentation processes according to the invention with respect to one or more of the parameters selected from the group of concentration (compound formed per volume), yield (compound formed per carbon source consumed), formation (compound formed per volume and time) and specific formation (compound formed per cell dry mass or bio dry mass and time or compound formed per cell protein and time) or other process parameters and combinations thereof, is increased by at least 0.5%, at least 1%, at least 1.5% or at least 2%, based on processes or fermentation processes with microorganisms in which the promoter variant according to the invention is present.

Owing to the measures of the fermentation, a fermentation broth is obtained which contains the desired fine chemical, preferably amino acid or organic acid.

Then, a product in liquid or solid form that contains the fine chemical is provided or produced or obtained.

A fermentation broth is taken to mean, in a preferred embodiment, a fermentation medium or nutrient medium in which a microorganism was cultured for a certain time and at a certain temperature. The fermentation medium, or the media used during the fermentation, contains/contain all substances or components that ensure production of the desired compound and typically ensure growth and/or viability.

On completion of the fermentation, the resultant fermentation broth accordingly contains a) the biomass (cell mass) of the microorganism resulting from growth of the cells of the microorganism,
b) the desired fine chemical formed in the course of the fermentation,
c) the organic by-products possibly formed in the course of the fermentation, and
d) the components of the fermentation medium used, or of the starting materials, that are not consumed by the fermentation, such as, for example, vitamins such as biotin, or salts such as magnesium sulphate.

The organic by-products include substances which are generated in addition to the respective desired compound by the microorganisms used in the fermentation and are possibly secreted.

The fermentation broth is withdrawn from the culture vessel or the fermentation container, optionally collected, and used for providing a product in liquid or solid form containing the fine chemical. The expression "obtaining the fine chemical-containing product" is also used therefor. In the simplest case, the fine chemical-containing fermentation broth withdrawn from the fermentation container is itself the product obtained.

By way of one or more of the measures selected from the group
a) partial (>0% to <80%) to complete (100%) or virtually complete ($\geq$80%, $\geq$90%, $\geq$95%, $\geq$96%, $\geq$97%, $\geq$98%, $\geq$99%) removal of the water,
b) partial (>0% to <80%) to complete (100%) or virtually complete ($\geq$80%, $\geq$90%, $\geq$95%, $\geq$96%, $\geq$97%, $\geq$98%, $\geq$99%) removal of the biomass, wherein this is optionally inactivated before the removal,
c) partial (>0% to <80%) to complete (100%) or virtually complete ($\geq$80%, $\geq$90%, $\geq$95%, $\geq$96%, $\geq$97%, $\geq$98%, $\geq$99%, $\geq$99.3%, $\geq$99.7%) removal of the organic by-products formed in the course of the fermentation, and
d) partial (>0%) to complete (100%) or virtually complete ($\geq$80%, $\geq$90%, $\geq$95%, $\geq$96%, $\geq$97%, $\geq$98%, $\geq$99%, $\geq$99.3%, $\geq$99.7%) removal of the components of the fermentation medium used or the starting materials that are not consumed by the fermentation, a concentration or purification of the desired organic chemical compound is achieved from the fermentation broth. In this manner, products are isolated that have a desired content of the compound.

The partial (>0% to <80%) to complete (100%) or virtually complete ($\geq$80% to <100%) removal of the water (measure a)) is also termed drying.

In a variant of the process, by complete or virtually complete removal of the water, the biomass, the organic by-products and the non-consumed components of the fermentation medium used, pure ($\geq$80% by weight, $\geq$90% by weight) or high-purity ($\geq$95% by weight, $\geq$97% by weight, $\geq$99% by weight) product forms of the desired organic chemical compound, preferably L-amino acids, are successfully arrived at. For the measures according to a), b), c) or d), a great variety of technical instructions are available in the prior art.

In the case of processes for producing KIC or L-leucine, using bacteria of the genus *Corynebacterium*, processes are preferred in which products are obtained that do not contain any components of the fermentation broth. These products are used, in particular, in human medicine, in the pharmaceuticals industry, and in the food industry.

The process according to the invention serves for the fermentative production of KIC or L-leucine.

The invention finally relates to use of the microorganism according to the invention for the fermentative production of KIC or L-leucine.

The present invention will be described in more detail hereinafter with reference to exemplary embodiments.

EXAMPLE 1

Production of the Exchange Vector
pK18mobsacB_leuA_Y553D

The synthesis of an 812 bp long exchange construct was performed at GeneArt (Life Technologies GmbH, Darmstadt, Germany) (see SEQ ID NO:7). The fragment contains the last 594 bp of the wild-type leuA gene (C terminus) to 206 bp of the downstream region of the leuA gene of ATCC13032, and also both the SphI and BamHI cutting sites required for cloning into the vector pK18mobsacB. At position 195, upstream of the 3' end of the leuA gene, in this exchange fragment the base T is mutated to the base G—this changes the wild-type codon TAC (encoding the amino acid Y, tyrosine) to the codon GAC (encoding the amino acid D, aspartate). Cloning the fragment into the vector pK18mobsacB was carried out at the company GeneArt. The resultant exchange vector pK18mobsacB_leuA_Y553D was delivered by GeneArt and used for producing the example strains (see Example 3).

EXAMPLE 2

Production of Strain C. glutamicum
ATCC13032_DilvE

Strain C. glutamicum ATCC13032 was transformed with the plasmid pK19mobsacB_DilvE (Marienhagen et al., Journal of Bacteriology 187:7639-7646 (2005)) by electroporation. The electroporation was carried out according to the protocol of Haynes et al. (FEMS Microbiology Letters 61: 329-334 (1989)).

The plasmid pK18mobsacB or pK18mobsacB_DilvE cannot replicate independently in C. glutamicum ATCC13032 and is only retained in the cell if, as a consequence of a recombination event, it has integrated into the chromosome. The screening of clones having an integrated pK18mobsacB_DilvE was carried out by plating out the electroporation batch on LB agar (Sambrook et al., Molecular Cloning: A Laboratory Manual, 2nd Ed., Cold Spring Habor, N.Y., 1989) which has been supplemented with 15 mg/l of kanamycin. Clones that grew were streaked onto LB agar plates containing 25 mg/l of kanamycin and incubated for 16 hours at 33° C. For screening mutants in which, as a consequence of a second recombination event, the plasmid has been excised, the clones were cultured for 20 hours unselectively in LB liquid medium (+5 g/l of potassium acetate), then streaked onto LB agar containing 10% sucrose and incubated for 24 hours.

The plasmid pK18mobsacB_DilvE contains, just like the starting plasmid pK18mobsacB, in addition to the kanamycin resistance gene, a copy of the sacB gene encoding the levan sucrase from Bacillus subtilis. The sucrose-inducible expression leads to the formation of levan sucrase which catalyses the synthesis of levan, the toxic product for C. glutamicum. On LB agar (containing 5 g/l of potassium acetate), with sucrose, therefore, only those clones grow in which the integrated pK18mobsacB has again been excised. In the excision, together with the plasmid, either the complete chromosomal copy of ilvE can be excised, or the incomplete copy with the internal deletion of ilvE.

Approximately 40 to 50 colonies were examined for the phenotype "growth in the presence of sucrose" and "non-growth in the presence of kanamycin". In order to detect that the deleted ilvE allele has remained in the chromosome, approximately 20 colonies which have the phenotype "growth in the presence of sucrose" and "non-growth in the presence of kanamycin" were studied according to the standard PCR method of Innis et al. (PCR Protocols. A Guide to Methods and Applications, 1990, Academic Press) using the polymerase chain reaction. In this case, from the chromosomal DNA of the colonies, one DNA fragment was amplified which carries the surrounding regions of the deleted ilvE region. The following primer oligonucleotides were selected for the PCR.

```
ilvE-XbaI-fw
5'-gctctagagccaagcctagccattcctcaa-3' ilvE-XbaI-rev
5'-gctctagagccagccactgcattctcctta-3'
```

The primers permit, in control clones having complete ilvE locus, the amplification of an approximately 1.4 kb size DNA fragment. In clones having a deleted argFRGH locus, DNA fragments having a size of approximately 0.6 kb were amplified.

The amplified DNA fragments were identified by electrophoresis in a 0.8% strength agarose gel. It could be shown thereby that the strain carries a deleted ilvE allele on the chromosome. The strain was termed C. glutamicum ATCC13032_DilvE and was studied in the production test (see Example 4) for its capability of producing isocaproate.

EXAMPLE 3

Production of the Strain C. glutamicum
ATCC13032_DilvE_leuAY553D and C. glutamicum
ATCC13032_leuAY553D The strain C. glutamicum ATCC13032 and strain C. glutamicum ATCC13032_DilvE from Example 2 were transformed by electroporation with the plasmid pK18mobsacB_leuA_Y553D from Example 1. The method is described in detail in Example 2.

Exchange of the wild-type codon TAC (encoding tyrosine at position 553) for the codon GAC (encoding aspartate at position 553) was demonstrated by sequencing a plurality of candidate clones of the phenotype "growth in the presence of sucrose" and "non-growth in the presence of kanamycin". For this purpose, first a PCR fragment of leuA-1 (767 bp long) having the primers leuA1 (5'-GATCTATCTAGAT-TGAGGGCCTTGGGCATACG-3') and leuA-2 (5'-GATCTAGGATCCGCGACTACGAGGCTGTTATC-3') was produced, and this was sequenced with the primer leuA-3 (5'-GATCTATCTAGAAAGCTTAAACGCCGCCAGCC-3'). Positive candidate clones were selected and examined in the subsequent performance test (Examples 4 and 5).

EXAMPLE 4

Production of ketoisocaproate with C. glutamicum
ATCC13032, C. glutamicum ATCC13032_DilvE and
C. glutamicum ATCC13032_DilvE_leuAY553D To study their ability to produce ketoisocaproate, the strains C. glutamicum ATCC13032, C. glutamicum ATCC13032_DilvE and C. glutamicum ATCC13032_DilvE_leuAY553D were precultured in 10 ml of test medium in each case for 16 h at 33° C. For the production test, each 10 ml of test medium were inoculated with the resultant preculture in such a manner that the starting OD 600 (optical density at 600 nm) was 0.1. Each clone was examined in three shake flasks in such a manner that each strain is represented by in total nine shake flasks. The test medium was identical to the CgXII medium described in Keilhauer et al. (Journal of Bacteriology (1993) 175: 5593-5603), but additionally contained in each case 200 mg/l of the amino acids L-leucine, L-valine and L-isoleucine. For the sake of simplicity, the composition of the test medium is summarized in Table 1 hereinafter.

TABLE 1

Composition of CgXII medium with addition of in each case 200 mg/l of the amino acids L-leucine, L-valine and L-isoleucine

| Component | Content per 1 |
|---|---|
| $(NH_4)_2SO_4$ | 20 g |
| Urea | 5 g |
| $KH_2PO_4$ | 1 g |
| $K_2HPO_4$ | 1 g |
| $MgSO_4 \cdot 7 H_2O$ | 0.25 g |
| 3-Morpholinopropane-sulphonic acid (MOPS) | 42 g |
| $CaCl_2$ | 0.01 g |
| $FeSO_4 \cdot 7H_2O$ | 0.01 g |
| $MnSO_4 \cdot H_2O$ | 0.01 g |
| $ZnSO_4 \cdot 7 H_2O$ | 0.001 g |
| $CuSO_4$ | 0.0002 g |
| $NiCl_2 \cdot 6H_2O$ | 0.00002 g |
| Biotin | 0.0002 g |
| Protocatechuic acid | 0.03 g |
| Glucose | 40 g |
| L-Valine | 0.2 g |
| L-Isoleucine | 0.2 g |
| L-Leucine | 0.2 g |
| pH (with NaOH) | 7 |

Culturing was carried out at 33° C. and 200 rpm in 100 ml shake flasks. The amplitude of the shaker was 5 cm. After 24 hours, samples were withdrawn from the cultures and the optical density was determined. Subsequently the cells were briefly centrifuged off (bench centrifuge type 5415D (Eppendorf) at 13 000 rpm, 10 min, room temperature) and the content of glucose and the content of ketoisocaproate were determined in the supernatant.

The optical density was determined at a wavelength of 660 nm using a GENios microtitre plate photometer (Tecan, Reading UK). The samples were diluted before measurement 1:100 with demineralized water. The analysis of KIC for determination of the concentration proceeds by separation of the keto acids and other secretion products by cation-exchange chromatography (REZEX RFQ—Fast Fruit H+ column (Phenomenex)) on a sulphonated styrene-divinylbenzene polymer in the H+ form using 0.025 N sulphuric acid with subsequent UV detection at 215 nm.

For calculation of the KIC yield, the amount of KIC formed was divided by the amount of dextrose consumed.

The results of the shake flask experiment for ketoisocaproate formation are shown in Table 2.

TABLE 2

Ketoisocaproate formation after 24 hours incubation.
Abbreviations: KIC = ketoisocaproate

| | Time 24 hours | | |
|---|---|---|---|
| Strain | KIC g/l | Yield g/g | OD |
| ATCC 13032 | 0 | 0 | 28.40 ± 1.10 |
| ATCC 13032_DilvE | 0.40 ± 0.03 | 0.012 ± 0.003 | 25.91 ± 0.81 |
| ATCC 13032_DilvE_leuAY553D | 1.09 ± 0.05 | 0.027 ± 0.004 | 25.71 ± 2.20 |

EXAMPLE 5

Production of L-leucine with C. glutamicum ATCC13032 and C. glutamicum ATCC13032_leuAY553D For investigation of their ability to produce leucine, the strains C. glutamicum ATCC13032 and C. glutamicum ATCC13032_leuAY553D were precultured in in each case 10 ml of test medium for 16 h at 33° C. The production test was carried out in a similar manner to Example 4, with the exception of an adaptation of the test medium which, for this test, did not contain the supplements leucine, valine and isoleucine. The test medium was identical to the CgXII medium described in Keilhauer et al. (Journal of Bacteriology (1993) 175: 5593-5603).

The optical density was determined at a wavelength of 660 nm using a GENios microtitre plate photometer (Tecan, Reading UK). The samples were diluted before measurement 1:100 with demineralized water. The amount of leucine formed was determined using an amino acid analyser from Eppendorf-BioTronik (Hamburg, Germany) by ion-exchange chromatography and post-column derivatization with ninhydrin detection.

In Table 3, the performance data obtained from the shake flask experiment on leucine formation are summarized.

For calculation of the leucine yield, the amount of leucine formed was divided by the amount of dextrose consumed.

TABLE 3

Leucine formation after incubation for 24 hours.

| | Time 24 hours | | |
|---|---|---|---|
| Strain | Leucine g/l | Yield g/g | OD |
| ATCC 13032 | 0.05 ± 0.01 | 0.002 ± 0.001 | 26.30 ± 1.10 |
| ATCC13032_leuAY553D | 1.55 ± 0.07 | 0.041 ± 0.004 | 23.55 ± 1.80 |

FIG. 1: Map of the plasmid pK18mobsacB_leuA_Y553D

The abbreviations and names used have the following meanings.
oriV: ColE1-like origin from pMB1
sacB: the sacB gene encoding the protein levansucrase
RP4-mob: RP4 mobilization site
Kan: resistance gene for kanamycin
leuA-3': 594 bp of the leuA gene (C terminus)

The invention claimed is:

1. An isolated polynucleotide encoding an α-isopropyl-malate synthase comprising an amino acid sequence that is at least 90% identical to the amino acid sequence of SEQ ID NO:2, wherein the amino acid sequence has a proteinogenic amino acid other than L-tyrosine at position 553 of SEQ ID NO:2 or at a corresponding position of the amino acid sequence.

2. An isolated polynucleotide encoding an α-isopropyl-malate synthase comprising an amino acid sequence that is at least 90%, identical to the amino acid sequence of SEQ ID NO:2, wherein the amino acid sequence has a proteinogenic amino acid other than L-tyrosine at position 553 of SEQ ID NO:2 or at a corresponding position of the amino acid sequence and the proteinogenic amino acid is selected from the group consisting of glutamic acid, aspartic acid, alanine, cysteine, serine, threonine, lysine, arginine, glutamine and asparagine.

3. The isolated polynucleotide according to claim 1, wherein the amino acid sequence encoded thereby has, at position 553 of SEQ ID NO:2 or at a corresponding position of the amino acid sequence, L-aspartic acid.

4. The isolated polynucleotide according to claim 1, having guanine at position 1657 of SEQ ID NO:5 or at a corresponding position of the polynucleotide.

5. The isolated polynucleotide according to claim 1, as depicted in SEQ ID NO: 5.

6. Vector comprising the isolated polynucleotide according to claim 1.

7. Vector comprising the isolated polynucleotide according to claim 2, which is suitable for replication in microorganisms of the genus *Corynebacterium*.

8. Polypeptide comprising an amino acid sequence encoded by the isolated polynucleotide according to claim 1.

9. Microorganism of the genus *Corynebacterium* comprising the isolated polynucleotide according to claim 1 or a polypeptide comprising an amino acid sequence encoded by said isolated polynucleotide or a vector comprising said isolated polynucleotide.

10. Microorganism according to claim 9, in which said isolated polynucleotide is present in overexpressed form as compared with a starting strain or wild-type strain.

11. Microorganism according to claim 9, wherein the isolated polynucleotide is integrated in a chromosome.

12. Microorganism according to claim 9, wherein it is *Corynebacterium glutamicum*.

13. Microorganism according to claim 9, wherein the microorganism has the capability of producing L-leucine or ketoisocaproate (KIC).

14. Fermentative process for producing KIC or L-leucine comprising the following steps:
   a) fermenting of one of the microorganisms according to claim 9 in a medium,
   b) accumulating the KIC or L-leucine in the medium, wherein a fermentation broth is obtained.

15. Process according to claim 14, wherein it is a process which is selected from the group consisting of batch process, fed-batch process, repetitive fed-batch process and continuous process.

16. Process according to claim 14, wherein the KIC or L-leucine is obtained from the fermentation broth.

17. A method for the fermentative production of L-leucine or KIC comprising culturing the microorganism of claim 9.

18. Microorganism of the genus *Corynebacterium* comprising the isolated polynucleotide according to claim 2 or a polypeptide comprising an amino acid sequence encoded by said isolated polynucleotide or a vector comprising said isolated polynucleotide.

19. Microorganism according to claim 18, in which said isolated polynucleotide is present in overexpressed form as compared with a starting strain or wild-type strain.

* * * * *